(12) United States Patent
Han et al.

(10) Patent No.: US 6,835,553 B2
(45) Date of Patent: Dec. 28, 2004

(54) PHOTOMETRIC GLUCOSE MEASUREMENT SYSTEM USING GLUCOSE-SENSITIVE HYDROGEL

(75) Inventors: In Suk Han, Salt Lake City, UT (US); Seok Lew, Salt Lake City, UT (US); Man Hee Han, Salt Lake City, UT (US)

(73) Assignee: M-Biotech, Inc., Sandy, UT (US)

( * ) Notice: Subject to any disclaimer, the term of this patent is extended or adjusted under 35 U.S.C. 154(b) by 202 days.

(21) Appl. No.: 10/120,870

(22) Filed: Apr. 11, 2002

(65) Prior Publication Data

US 2002/0155425 A1 Oct. 24, 2002

Related U.S. Application Data

(63) Continuation-in-part of application No. 09/839,993, filed on Apr. 20, 2001, now Pat. No. 6,514,689, which is a continuation-in-part of application No. 09/644,323, filed on Aug. 23, 2000, now Pat. No. 6,475,750, which is a continuation-in-part of application No. 09/308,392, filed on May 11, 1999, now Pat. No. 6,268,161.
(60) Provisional application No. 60/341,677, filed on Dec. 17, 2001.

(51) Int. Cl.$^7$ .............................. C12G 1/54; C12M 1/34
(52) U.S. Cl. ........................ 435/14; 435/25; 435/288.7; 359/290; 436/95; 436/148
(58) Field of Search ............................... 435/288.7, 14, 435/25, 287.1; 359/290, 886, 296; 436/95, 148; 604/891.1, 892.1; 356/334; 252/582

(56) References Cited

U.S. PATENT DOCUMENTS

| | | |
|---|---|---|
| 4,703,756 A | 11/1987 | Gough et al. |
| 5,898,004 A * | 4/1999 | Asher et al. ................. 436/518 |
| 6,268,161 B1 | 7/2001 | Han et al. |

OTHER PUBLICATIONS

Bouin, J.C., Atallah, Mokhtar T., and Hultin, Herbert O., "Parameters in the Construction of an Immoblized Dual Enzyme Catalyst," Biotechnology and Bioengineering, 1976, p. 179–187, vol. XVIII.

Chen, L.H., "Kinetic Modeling for Macromolecule Loading into Crosslinked Polyacrylamide Hydrogel Matrix by Swelling," Pharmaceutical Development and Technology, 1998, p. 241–249, vol.3(2).

Gough, D.A., Lucisano, J.Y., and Tse, P.H.S., "Two–Dimensional Enzyme Electrode Sensor for Glucose," Analytical Chemistry, 1985, p. 2351–2357, vol. 57.

Guillbault, G.G., Suleiman, A.A., Fatibello–Filho, O., Nabirahni, M.A., Bioinstrumentation and Biosensors, 1991, p. 664–692, D.L. Wise ed., Marcel Dekker.

(List continued on next page.)

Primary Examiner—David A Redding
(74) Attorney, Agent, or Firm—Mallinckrodt & Mallinckrodt; Robert R. Mallinckrodt

(57) ABSTRACT

An implantable biosensor for detecting an analyte in vivo in body fluids comprises an analyte-sensitive hydrogel filament chemically configured to vary its displacement volume according to changes in concentration of an analyte, such as glucose, in a patient's body fluid. A photometric displacement transducer placed inside the biosensor is configured to quantifiably detect changes in the displacement volume of the hydrogel filament, such as by detecting the light intensity on a photoreceptor arranged to receive light of varying intensity depending upon the displacement of the hydrogel filament. A battery powered telemeter operably engaged to the photometric displacement transducer sends a radio data signal representing glucose concentration level to a receiver containing an alarm system. The alarm system can automatically notify a person that the analyte level is outside desired predetermined parameters, and/or to automatically inject an agent to counteract the adverse analyte levels.

40 Claims, 25 Drawing Sheets

OTHER PUBLICATIONS

Hill, D.J.T., Moss, N.G., Pomery, P.J., Whittaker, A.K., "Copolymer hydrogels of 2-hydroxyethyl methacrylate with n-butyl methacrylate and cyclohexyl methacrylate: synthesis, characterization and uptake or water," Polymer, 2000, p. 1287–1296, vol. 41.

Ishihara, K., Kobayashi, M., Shionohara, I., "Control of Insulin Permeation through a Polymer Membrane with Responsive Function for Glucose," Makromo. Chem., Rapid Commun., 1983, p. 327–331, vol. 4.

Ishihara, K., Kobayashi, M., Shionohara, I., "Glucose Induced Permeation Control of Insulin through a Complex Membrane Consisting of Immoblized Glucose Oxidase and Poly(amine)," Polymer Journal, 1984, p. 625–631, vol. 16 No. 8.

Khare, A.R., Peppas, N.A., "Release behavior of bioactive agents from pH–sensitive hydrogels," Biomaterials, 1995, p. 559–567, vol. 21.

Krysteva, M.A., Yotova, L.K., "Multienzyme Membranes for Biosensors," J. Chem. Tech. Biotechnol., 1992, p. 13–18, vol. 54.

Lee, C.S., Magda, J.J., and Devries, K.L., "Measurements of the Second Normal Stress Difference for Star Polymers with Highly Entangled Branches," Macromolecules, 1992, p. 4744–4750, vol. 25.

Lee, C.S., Tripp, B.C., Magda, J.J., "Does N1 or N2 control the onset of edge fracture?" Rheologica Acta, 1992, p. 306–308, vol. 31.

Lee, K.K., Cussler, E.L., "Pressure–dependent phase transitions in hydrogels," Chemical Engineering Science, 1990, p. 766–767, vol. 45. No. 3.

Lucisano, J.Y., Gough, D.A., "Transient Respose of the Two–Dimensional Glucose Sensor," Analytical Chemistry, 1988, p. 1272–1281, vol. 60, No. 13.

Magda, J.J., Baek, S.G., Devries, K.L., and Larson, R.G., "Unusual pressure rofiles and fluctuations during shear flows of liquid crystal polymers," Polymer, 1991, p. 1794–1797, vol. 32, No. 10.

Magda, J.J., Baek, S.G., Devries, K.L., Larson, R.G., "Shear flow of liquid crystal polymers: measurememtns of the second normal stress difference and the doi molecule theory," Macromolecules, 1991, p. 4460–4468, vol. 24.

Magda, J.J., Lou, J., Baek, S.G., and Devries, K.L., "Second normal stress difference of a Boger fluid," Polymer, 1991, p. 2000–2009, vol. 32.

Malikkides, C.O., Weiland, R.H., "On the Mechanism of Immobilized Glucose Oxidase Deactivation by Hydrogen Peroxide," Biotechnologyand Bioengineering, 1982, p. 2419–2439, vol. XXIV.

Mays, J.W., Nan, S., Yunan, W., and Li, J., "Temperature Dependence of Chain Dimensions for Highly Syndiotactic Poly(methyl methacrylate)," Macromolecules, 1991, p. 4469–4471, vol. 24.

Obaidat, A.A., and Park, K., "Characterization of protein release through glucose–sensitive hydrogel membranes," Biomaterials, 1997, p. 801–806, vol. 18.

Rao, J.K., Ramesh, D.V., and Rao, K.P., "Implantalbe controlled delivery systems for proteins based on collagen—pHEMA hydrogels," Biomaterials, 1994, pp 383–389, vol. 15, No. 5.

Schott, H., "Kinetics of Swelling of Polymers and Their Gels," Journal of Pharmaceutical Sciences, 1992, p. 467–470, vol. 81, No. 5.

Teijon, J.M., Trigo, R.M., Garcia O., and Blanco, M.D., "Cytarabine trapping in poly(2–hydroxyethyl methacrylate) hydrogels: drug delivery studies," Biomaterials, 1997, p. 383–388, vol. 18.

Updike, S.J., Shults, M.C., Thodes, R.K., Gilligan, B.J., Luebow; J.O., and Von Heimburg, D., "Improved Long–Term Performance In Vitro and In Vivo," ASAIO Journal, 1994, p. 157–163.

Wilkins, E.S., "Towards implantable glucose sensors: a review," J. Biomed. Eng., 1989, p. 354–361, vol. 11.

Yoshitake, S., Imagawa, M., Ishikawa, E., et al, "Mild and Efficient Conjugation of Rabbit Fab' and Horseradish Peroxidase Using a Maleimide Compound and Its Use for Enzyme Immunoassay," J. Biochem, 1982, p. 1413–1424, vol. 92.

Yoshitake, S., Imagawa, M., Ishikawa, E., "Efficient Preparation of Rabbit Fab'–Horseradish Peroxidase Conjugates Using Maleimide Compound and its use for Enzyme Immunoassay," Analytical Letters, 1982, p. 147–160, vol. 15(B2).

* cited by examiner

PHOTOMETRIC GLUCOSE MEASUREMENT SYSTEM USING GLUCOSE-SENSITIVE HYDROGEL

RELATED APPLICATIONS

The present application is a continuation-in-part of application Ser. No. 09/839,993, filed Apr. 20, 2001, now U.S. Pat. No. 6,514,689, which is a continuation-in-part of Ser. No. 09/644,323, filed Aug. 23, 2000, now U.S. Pat. No. 6,475,750, which is a continuation-in-part of Ser. No. 09/308,392, filed on May 11, 1999, now U.S. Pat. No. 6,268,161, and claims the benefit of Provisional Patent Application Ser. No. 60/341,677, filed Dec. 17, 2001, and entitled "Photometric glucose measurement system using glucose-sensitive hydrogel and health alarm system".

BACKGROUND OF THE INVENTION

1. Field of Invention

This invention relates generally to biosensors for measuring physiological analytes in humans, and particularly to biosensors suitable for implantation to provide in vivo monitoring of a selected analyte, such as monitoring of blood glucose levels in diabetics.

2. Description of Related Art

For some time the medical community has recognized a need for implantable biosensors to monitor physiologically important analytes. The need is particularly pressing for continuous monitoring of blood glucose in diabetics, since failure to properly maintain glucose levels leads to serious consequences in both the short and long term. The long-term consequences include kidney failure, blindness, and amputation. To date, however, the only test readily available is a fingerstick kit, which does not provide continuous monitoring. Most diabetics use such kits infrequently at best, because of the pain and inconvenience associated with them.

In developing various implantable devices, hydrogels have been widely used as protective biocompatible coatings for the devices. Hydrogels are generally defined as polymeric materials that swell in water and other fluids, absorbing the fluid within the polymer network without dissolving. Hydrophilic hydrogels have a large amount of water content at equilibrium, and good biocompatibility.

The above-described properties of hydrogels make them attractive for use in implantable biosensors. One such device is an implantable amperometric sensor intended to measure glucose levels in blood or body fluids (U.S. Pat. No. 4,703,756 to Gough et al.). A second type of hydrogel biosensor which uses a pressure transducer to measure changes in osmotic pressure in pH-sensitive hydrogels, developed by the present inventors, is described in U.S. Pat. No. 6,268,161 to Han et al., and in co-pending U.S. patent application Ser. Nos. 09/308,392 and 09/644,323.

The Gough et al. biosensor uses the enzymatic activity of glucose oxidase (GOX) to measure glucose levels. GOX catalyzes the conversion of glucose to gluconic acid and hydrogen peroxide ($H_2O_2$), consuming oxygen in the process. The GOX reaction can be followed using electrochemical transducers of various kinds, but the most advanced type of device is the amperometric sensor. In the amperometric method, an electrode produces a current proportional to the diffusional flux of hydrogen peroxide to the electrode surface, or, alternatively, proportional to the diffusional flux of oxygen ($O_2$) to the electrode surface. An increase in the surrounding glucose concentration should increase the diffusional flux of glucose into the membrane and increase the reaction rate within the membrane. The increase in enzymatic reaction rate in turn should increase the local hydrogen peroxide concentration and decrease the local oxygen concentration within the membrane. This increases the current detected by a hydrogen peroxide-based electrode sensor, or decreases the current to an oxygen-based electrode sensor. The latter approach, based on detecting the oxygen flux, requires a reference oxygen-based electrode sensor located in a hydrogel without the enzyme.

A second class of osmotic-pressure hydrogel sensors uses a pressure transducer to directly measure osmotic pressure changes in a hydrogel disposed within a rigid chamber having one open side which is covered with a flexible, semi-permeable diaphragm (Han et al., U.S. Pat. No. 6,268,161; Han et al., U.S. application Ser. Nos. 09/839,993 and 09/644,323). The pressure transducer senses changes in the pressure exerted by the hydrogel on the flexible diaphragm. Two types of such sensors have been developed. One uses pH-sensitive hydrogels having immobilized GOX. In this device, the gluconic acid produced by enzymatic action of GOX on free glucose changes the pH in the fluid matrix, causing it to swell (if the hydrogel has pendant acidic groups) or to shrink (if the hydrogel has pendant basic groups). The second type, which has potentially far wider application, uses the principles of the competitive binding assay. Both analyte and analyte-binding molecules are immobilized within the hydrogel; noncovalent bonds between the two effectively produce crosslinks. When free analyte displaces immobilized analyte, the crosslinking index changes, producing either swelling or shrinking of the hydrogel (depending on other factors in hydrogel composition). The resulting changes in osmotic pressure are measured with a pressure transducer in the same way as for the GOX osmotic-pressure biosensor. Where the analyte is glucose, the immobilized analyte binding molecule may for example be concanavalin A.

In addition to the above-described biosensors, there is another hydrogel-based glucose measurement system that measures the displacement change of the hydrogel in the pending U.S. Provisional Patent Application Ser. No. 60/316731 to Lew et al. and in co-pending U.S. patent application Ser. No. 10/054660. The swelling displacement of the implanted hydrogel is monitored by image capture from outside the body such as an ultrasound scanning device, and the change of displacement characterizes the glucose concentration.

SUMMARY OF THE INVENTION

The present invention comprises a hydrogel-based biosensor that measures the displacement of an analyte-sensitive hydrogel filament such as glucose-sensitive hydrogel filament (GSF). In order to measure the displacement, the hydrogel filament is placed in a rigid column that has at least one semi-permeable opening to permit contact between the hydrogel filament and the test fluid (a patient's blood or other solution), and a photometric displacement detection means is provided for detecting the displacement of the hydrogel filament.

Two types of specially chemically configured hydrogels are presently preferred for use in the invention. In one, an oxidative enzyme is immobilized within a pH-sensitive hydrogel, and catalyzes a reaction of the analyte to produce a charged product. The term 'pH-sensitive hydrogel' refers generally to a hydrogel modified to contain pendant charged groups in proportions that produce an overall acidic or basic environment in the fluid within the gel. The immobilized enzyme might be, for example, glucose oxidase, GOX, where the analyte to be measured is glucose. The charged product generated by activity of the enzyme on the analyte causes the hydrogel to change its displacement volume (swell or shrink), which changes can be detected by the displacement detection means. The second type of hydrogel has both analyte binding molecules (ABMs) and analyte or analyte analogue molecules (AAMs) co-immobilized within it, in addition to charged pendant groups. In the absence of free analyte, immobilized ABMs bind to immobilized AAMs, forming what are in effect non-covalent 'crosslinks'. As free analyte from a body fluid or test solution diffuses into the hydrogel, binding competition displaces immobilized AAMs from ABMs, thus reducing the number of 'crosslinks'. This reduction in crosslinking causes swelling of the hydrogel.

Also, in addition to the above two types of hydrogels, it is within contemplation that other analyte-sensitive swellable materials, polymers, and hydrogels meeting that description may be developed and will be useful in the biosensor. Certain embodiments of the invention are specifically designed to detect glucose levels in body fluids.

In its broadest conception, the invention is an implantable analyte (for example, glucose) biosensor containing an analyte-sensitive hydrogel filament and a photometric displacement transducer. The displacement of the hydrogel filament changes with changes in the concentration of the analyte. A set of a light source and light intensity detector (photoreceptor) measures the displacement of the hydrogel by detecting changes of intensity of light that falls on the detector: the intensity of light received is converted to an electric signal. In a preferred embodiment, a photo diode and a phototransistor are the light source and the light intensity detector, respectively. Such a biosensor comprises a rigid biocompatible enclosure having one or more openings permitting penetration of a patient's body fluid to the hydrogel. The hydrogel filament is preferably disposed within a column in the enclosure and is configured to swell freely in only one dimension relative to a fixed end.

The hydrogel is chemically configured to vary its displacement volume according to changes in concentration of the particular analyte to be measured, such as glucose, in the body fluid, and is positioned, such as between the light source and the light intensity detector, so that the light falling on the light intensity detector is determined by the displacement of the hydrogel.

If desired, the biosensor and the hydrogel can be fabricated in a micro level. Brock et al. describe attempts to make artificial muscle from bundles of extremely thin (10 micron diameter) polyacrylonitrile fibers ("Dynamic Model of Linear Actuator based on Polymer Hydrogel", published on the Web at www.ai.mit.edu/projects/muscle/papers/icim94). In addition, modem optical MEMS technology permits the photometric devices such as a photo LED and a photo detector to be fabricated in a micro level. Those who are skilled in these fields can accommodate a miniaturized photometric glucose biosensor based on the proposed idea and the up-to-date technology.

The invention further encompasses methods of determining the concentration of free analyte in a solution and of making the biosensor. The method of determining analyte concentration comprises steps of: providing a hydrogel in a manner so that the displacement of the hydrogel changes depending upon the concentration of the analyte being measured and detecting the displacement of the hydrogel using a photometric detector where light sensed by a photoreceptor indicates hydrogel displacement. Further, the method may include providing a hydrogel having pendant charged and/or uncharged moieties, analyte molecules, and analyte-specific binding molecules covalently immobilized therein; contacting the hydrogel sequentially with a series of calibration solutions having known concentrations of free analyte, and measuring the displacement of the hydrogel for each of the calibration solutions to produce a calibration curve of displacement versus analyte concentration; contacting the hydrogel with the test fluid, and measuring a resulting displacement; and comparing the resulting displacement with the calibration curve to determine the analyte concentration of the test fluid. A further embodiment of the method includes a step of enclosing the hydrogel in a rigid structure which has at least one permeable portion through which free analyte in the test solution can diffuse into the hydrogel, with the structure sized and configured to permit hydrogel expansion in substantially only one dimension. Limiting the hydrogel expansion and contraction to substantially only one dimension makes the measurement of displacement more sensitive.

A further embodiment of the biosensor includes reporting means associated with the displacement detection means for reporting a data signal reflective of hydrogel displacement, and computing means operably disposed to receive the data signal and constructed to compare it to a predetermined limit and to produce a warning or alarm notification if at that predetermined limit. In a preferred embodiment, the reporting means is a battery-powered telemeter that sends a radio data signal to a receiver operably attached to the computing means. In a further preferred embodiment, the computing means is associated with an alarm system. The computing means may be a personal computer, but in a preferred embodiment, the computing means is a microprocessor. In a more highly preferred embodiment, the computing means contains or is operably associated with alarm means for providing an alarm signal when the analyte concentration falls outside a pre-determined acceptable range. In a further highly preferred embodiment, the biosensor unit carried in or on the patient's body includes a GPS (global positioning system) unit.

Thus, a further invention described herein comprises biosensor-based health alarm system which provides a warning of an adverse condition detected by a biosensor to care providers at a location remote to the patient via telephone or wireless transmission means. In a highly preferred embodiment, the system includes a GPS unit and a wireless phone, thus providing monitoring and alarm coverage to the patient while traveling. The biosensor of the system may be any sensor configured to detect a critical health-related biological determinant (such as, but not limited to, the concentration of a selected analyte, such as glucose in the patient's body fluid). The system may further include an automatic drug administration component that responds to the sensor by administering an appropriate amount of a drug to ameliorate the adverse effects of the change in the biological determinant.

BRIEF DESCRIPTION OF THE DRAWINGS

The above and other objects, features and advantages of the invention will be apparent from a consideration of the following detailed description presented in connection with the accompanying drawings in which.

DETAILED DESCRIPTION OF THE ILLUSTRATED EMBODIMENTS

While the invention can be used to measure the concentration of various analytes in various fluids, the invention will be described with reference to measuring glucose in body fluids. For measuring other analytes, hydrogels which respond to the specific analytes to be measured, should be used.

Figure 1:
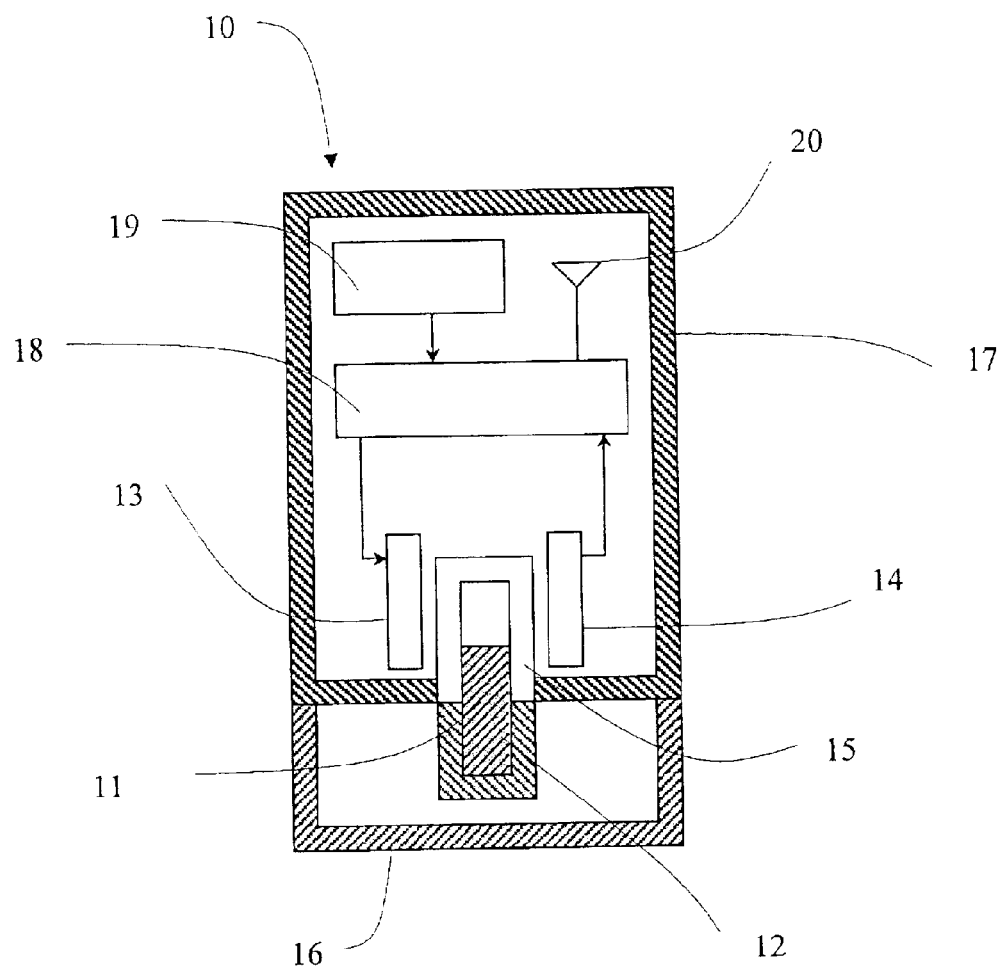
FIG. 1 shows schematically a design of a photometric biosensor.

FIG. 1 shows one embodiment of the photometric glucose biosensor of the invention. A glucose biosensor 10 consists of a glucose-sensitive hydrogel and a photometric displacement transducer mounted in a housing. The glucose-sensitive hydrogel 11 is preferably fabricated as a thin filament, which gives a faster swelling response due to its easiness to be infused. One end of the hydrogel filament 11 is contained in a column made of a semi-permeable material 12 and the other end is positioned in a rigid non-permeable transparent material. The semi-permeable portion 12 of the column enables body fluid to permeate to the hydrogel so that the hydrogel filament swells along the inside of the column in an amount determined by the glucose level in the body fluid. The hydrogel is preferably bonded with an epoxy on the bottom of the semi-permeable column so that the hydrogel is displaced only in the upper direction. The non-permeable transparent portion 15, which is a part of rigid non-permeable transparent container 17, is designed to allow the hydrogel to be exposed to incoming light from a light source 13, so that a light intensity detector 14, which serves as a photoreceptor, can measure the intensity of the light passing through the portion 15 and falling on detector 14. As the hydrogel 11 swells and expands into portion 15, it will block a portion of the light passing through portion 15 so that less light falls on detector 14. As the hydrogel contracts, it will allow more light to pass through portion 15 and fall on detector 14. Thus, the intensity of the light from light source 13 that is detected by detector 14 is a measure of the displacement of hydrogel 11 in portion 15 which is caused by and is then a measure of the concentration of glucose in the body fluid being tested. In this particular embodiment, an infrared photo diode with a wavelength of 800 nm to 850 nm is preferably used as the light source 13, and a phototransistor with a built-in visible light filter is preferably used as infrared light intensity detector 15. An infrared light source and infrared light detector allow operation of the biosensor in varying visible light conditions, i.e. the visible light conditions do not affect the measurement obtained, although visible light will not generally be a consideration when the biosensor is implanted into a body. The non-permeable transparent material for the column 15 is preferably polyacrylonitrile, polymethylmethacrylate, or polycarbonate. The semi-permeable part of the column 12 is preferably protected against bending and breakage due to physical interference such as through muscle movement by a rigid permeable enclosure 16. The electronic circuitry 18 with the photo diode 13 and the phototransistor 14 are enclosed in a rigid non-permeable container 17, so that the electronic components are protected against failure due to body fluid. The electronic circuitry acquires operating power from a battery 19. The electronic circuitry 18 will generally output or report a data signal reflective of the measured light intensity on the photoreceptor, here phototransistor 14. However, the circuitry 18 could include computing circuitry or means such as microprocessor responsive to the data signal to produce a determination of the glucose level. The electric signal from circuitry 18 is exported to an outside computing means, readout device, or monitoring device by a wireless means 20. Rather than relying on battery power, a computing means, a readout device, or monitoring device can supply power to the biosensor and acquire biosensor signals by a wire connection, if desired.

Figure 2:
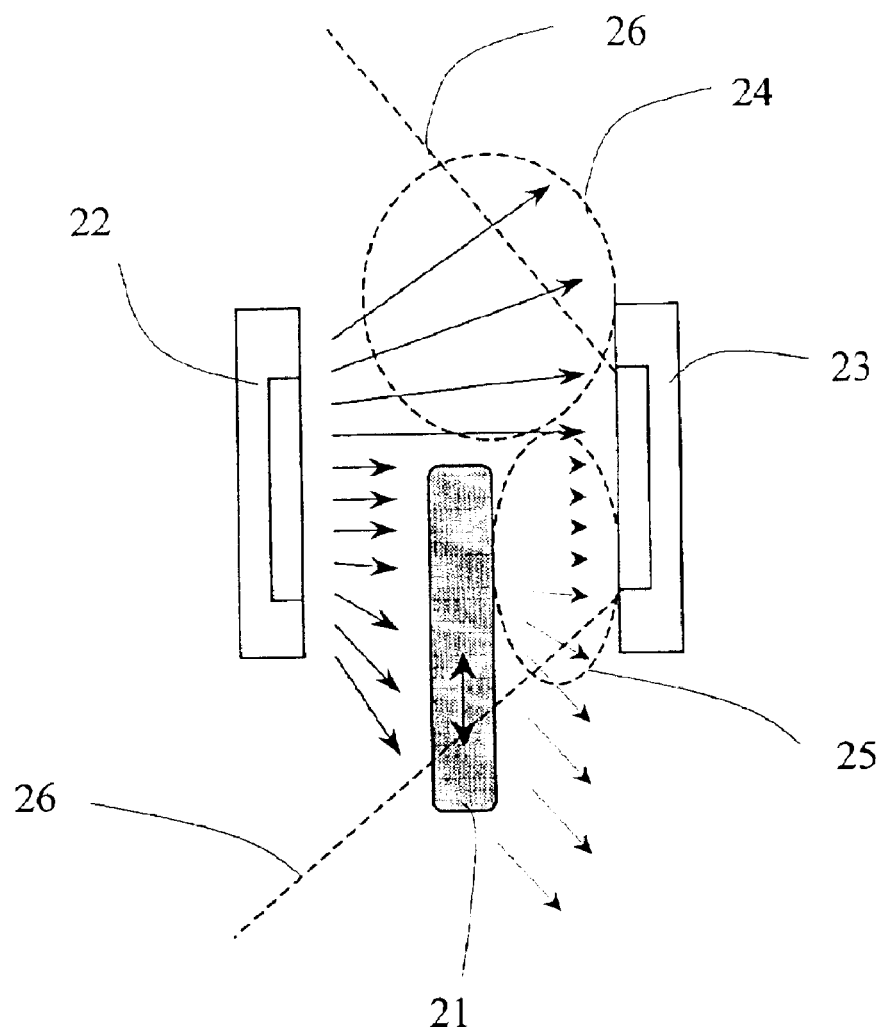
FIG. 2 shows a principle of photometric displacement measurement.
Figure 3:
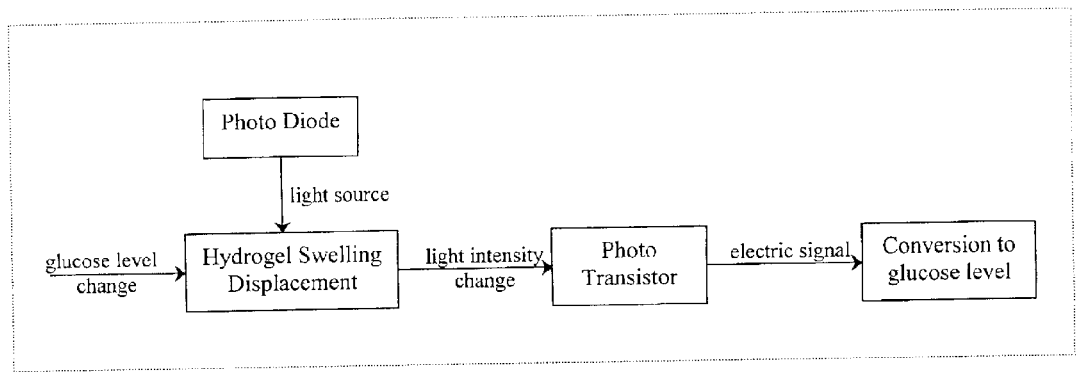
FIG. 3 is a flow chart showing the principle of photometric glucose measurement.

FIG. 2 shows the principle of the photometric glucose biosensor. The glucose-sensitive hydrogel 21 swells in a proportional amount depending on the glucose level change in body fluid. One side of the hydrogel is exposed to the infrared light source of photo diode 22 so that the hydrogel blocks the incoming light and absorbs the energy in a proportional amount of the hydrogel length change. The hydrogel is preferably dyed to block and absorb the incoming light. The light intensity detector of phototransistor 23 measures the intensity of arriving light consisting of the attenuated light due to the energy absorption of the hydrogel 25 and the direct light from the light source 24. Accordingly, the hydrogel responding to glucose level changes provides proportional light intensity changes, and the phototransistor 23 converts the detected light intensity into a corresponding electric signal, which represents glucose concentration level. The photo diode emits the infrared light within certain illuminating angle from the center of diode, and the phototransistor accepts the incoming light within certain reception angle 26, so that the hydrogel is preferably placed within the light field made by photo diode 22 and detected by phototransistor 23. FIG. 3 shows the principle of photometric glucose measurement in the form of block diagram.

Glucose-Sensitive Hydrogel Filament (GSF)

Hydrogels are defined as polymeric materials that swell in water and other solvents, absorbing the fluid within the polymer network without dissolving. Hydrophilic hydrogels have a large amount of water content at equilibrium and good biocompatibility. Hydrogels can be made sensitive to particular analytes, such as glucose. The invention will be further described in relation to glucose sensitive hydrogels wherein the biosensor takes the form of a glucose sensor. However, the principles and operation of the biosensor will be the same for hydrogels sensitive to other analytes.

There are several ways to make a hydrogel sensitive to glucose. A glucose-sensitive hydrogel will be referred to as GSF. The first type of GSF contains immobilized GOX within pH-sensitive hydrogels, which are copolymers synthesized from various types of methacrylate-derived monomers by free radical solution polymerization. These copolymers are tough, flexible polymers rather than soft hydrogels and are highly biocompatible and inert yet nondegradable in vivo.

A pH-sensitive co-polymeric hydrogel that contains immobilized GOX acts as a sensor of glucose via the conversion of glucose to gluconic acid by the enzyme. The rate of gluconic acid formation is proportional to the glucose concentration in the hydrogel at the reaction location. The changes in glucose concentration in the fluid surrounding the hydrogel result in the changes in the pH value within the hydrogel due to the GOX-catalyzed production of gluconic acid. The gluconic acid protonates pH-sensitive pendant groups in the hydrogel and causes the hydrogel to swell or de-swell, depending on the nature of the pendant groups. If the hydrogel contains basic pendant groups such as diethylaminoethyl methacrylate (DEAMA), it will swell when pH decreases. If it contains acidic pendant groups such as acrylic acid (AA), the hydrogel will shrink when pH decreases. If the GSF is allowed to expand or contract within only one dimension, as is the case for the filament in a rigid or semi-rigid support block, then filament length depends directly on glucose concentration near the hydrogel.

Figure 4:
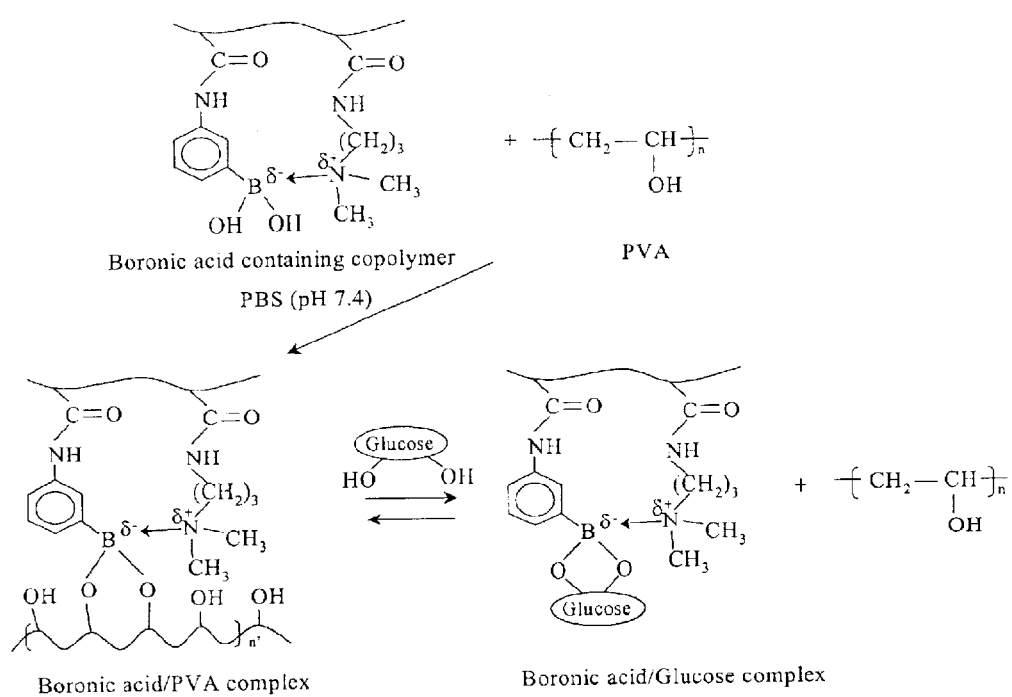
FIG. 4 depicts a competitive binding-type hydrogel based on phenylboronic acid.
Figure 5:
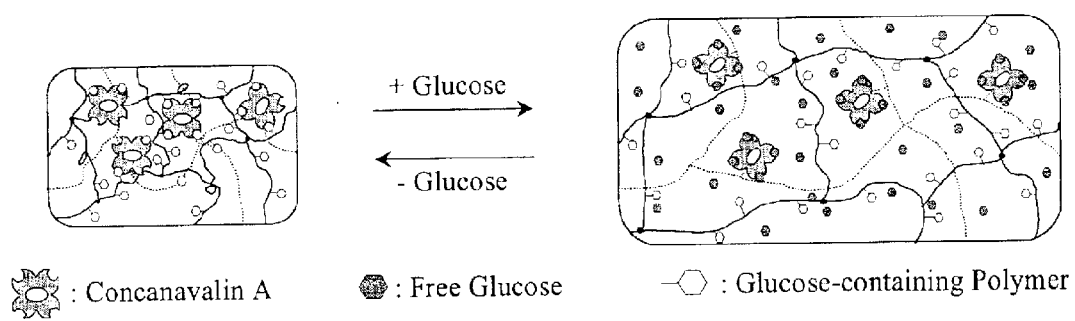
FIG. 5 depicts a competitive binding-type hydrogel based on Concanavalin A, and its swelling mechanism.
Figure 6:
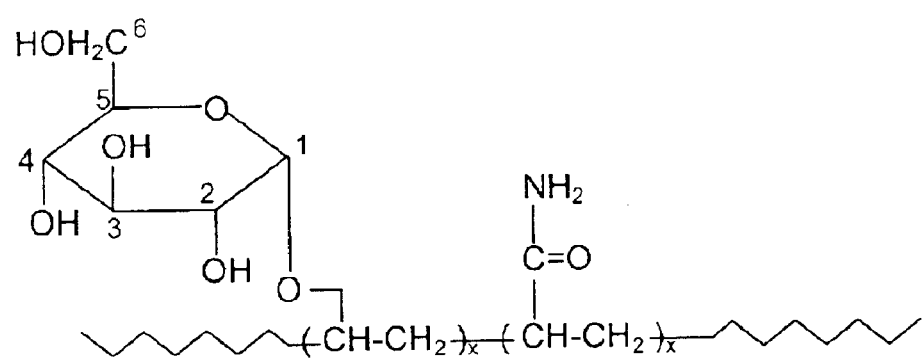
FIG. 6 is an example of vinyl group conjugated glucose.

The second type of GSF is based on a competitive mechanism and does not require oxygen-consuming enzymatic reactions (FIGS. 4, 5). This GSF preferably contains immobilized phenylboronic acid, FIG. 4, (or other glucose binding molecules with a non-covalent bond such as lectins in FIG. 5), which form covalent crosslinks within the diols on the polyols in the hydrogel (FIG. 6). The volume of this hydrogel changes with free glucose concentration due to a competitive binding effect to phenylboronic acid with a covalent bond or other GBM with a noncovalent bond. When the glucose concentration increases near the implant area, additional amounts of free glucose diffuse into the hydrogel and displace polyols from the binding sites of the immobilized phenylboronic acid (FIG. 4). This reduces the hydrogel crosslink density, and thus the hydrogel swells. This type of GSF eliminates problems with pH-sensitive hydrogels such as oxygen deficit and enzyme degradation that have hindered the development of implantable electrochemical glucose sensors using pH-sensitive hydrogels.

Optimization of GSF for Glucose-Dependent Elongation

The optimization of GSF for glucose-dependent elongation depends upon these factors: the target range of glucose concentrations, the required degree of accuracy, hydrogel composition, and the size of the filament. Except for hydrogel composition and degree of accuracy, most of these factors are easily estimated beforehand. The glucose-sensitive hydrogel is preferably designed to measure blood glucose concentration with a degree of accuracy of 20 mg/dL or better. The length of the hydrogel filament is preferably less than 1 cm, and the target glucose concentration range of the sensor is preferably between 50 mg/dL to 450 mg/dL with a less than 20 mg/dL increment. Response time is preferably within a few minutes. The hydrogel slab may be a single piece of hydrogel or made up of a plurality of pieces of hydrogel. A micro fiber of hydrogel or a bundle of micro fibers can be used in order to provide a faster response time.

Synthesis of a GSF Based on GOX Immobilization

Synthesis conditions for pH-sensitive hydrogels have been well established. Based on these previous studies, we preferably use acrylamide (AM) or dimethylacrylamide (DmAM) as a polymer backbone, sodium acrylate (NaAA) as the pH-sensitive pendant group, and N, N'-methylene-bis-acrylamide (MBA) as the crosslinker. To obtain the acidic hydrogel copolymers with different properties, the ratios of the monomers and MBA cross-linker are preferably varied as shown in TABLE 1.

TABLE 1

Relative amounts of reactants in each hydrogel

| Component | Mole ratio (%) of reactants (Sodium acetate buffer pH5, 25° C.) | | | | |
|---|---|---|---|---|---|
| | Reaction 1 | Reaction 2 | Reaction 3 | Reaction 4 | Reaction 5 |
| AM | 70 | 50 | 30 | 70 | 70 |
| NaAA | 30 | 50 | 70 | 30 | 30 |
| MBA | 2.0 | 2.0 | 2.0 | 1.5 | 1.0 |
| APS | 0.001 | 0.001 | 0.001 | 0.001 | 0.001 |
| TEMED | 0.003 | 0.003 | 0.003 | 0.003 | 0.003 |

Each reaction preferably takes place by free radical solution polymerization in a 20 ml flask at ambient temperature. A total 5 g of monomers and cross-linker are preferably dissolved in 10 ml of sodium acetate (pH 5.0) buffer to dissolve pendant groups in a 20 ml flask. The polymerization mixture is thoroughly mixed for 10 min, and is then bubbled with argon gas to remove oxygen for 20 min in an ice bath. Polymerization and cross-linking is preferably achieved by adding an initiator ammonium persulfate (APS), preferably in an amount of about 1%. The mixture solution is poured between two glass plates and kept at 4° C. until polymerization is completed. The glass plates are separated with spacers in order to obtain gels of desired thickness. After completion of the reaction, the gel is washed 3 times with PBS buffer ([I]=0.15) and stored at 4° C. in PBS buffer until use. The above procedure provides a pH sensitive hydrogel that is not sensitive to any particular analyte, and which may be useful in the invention as a reference hydrogel.

To make the hydrogel glucose sensitive, GOX enzymes and catalase are added. The enzymes GOX and catalase are introduced during the reaction stages which result in physical immobilization of the enzymes within the hydrogel. The amount of GOX varies between 20 and 200 mg per 10 ml of polymerization mixture; the GOX (Sigma products) contains a fixed weight fraction of catalase. Additional catalase is added as a quencher of hydrogen peroxide in order to decrease peroxide-mediated GOX deactivation, which would limit the useful life of the hydrogel.

In our studies thus far, thin pH-sensitive hydrogels show faster kinetic volume change than thick hydrogels. The hydrogels also show good reversibility for cyclic changes in salt, pH, and glucose concentrations.

Synthesis of a Series of GSF Based on a Competitive Binding Mechanism with Covalent Bind To produce a competitive binding hydrogel, glucose-conjugated and GBM (Glucose Binding Molecule)-conjugated vinyl monomers are synthesized. These conjugated monomers are then co-polymerized with crosslinkers and either cationic or anionic monomers. The crosslinker introduces a small number of permanent crosslinks into the hydrogel in order to keep hydrogel integrity at all free glucose concentrations.

This novel type of GSF contains immobilized GBM and polyols such as poly(vinyl alcohol) (PVA), with other pendant groups as necessary to achieve the desired sensitivity, response, and durability. The GBM is preferably a phenylboronic acid having a high binding affinity and binding specificity for saccharides such as glucose. The volume of this hydrogel responds to the environmental concentration of free glucose via a competitive binding mechanism that is very specific and does not require oxygen or enzymes. When immobilized GBM reversibly binds to diol groups of polyols, it creates crosslinks in the hydrogel that act to resist hydrogel swelling.

As shown in FIG. 4, when the concentration of glucose in the solution surrounding the hydrogel increases, free glucose diffuses into the gel and displaces diol moieties from the binding sites of the GBM, thereby decreasing the density of crosslinks in the hydrogel. Since hydrogel volume has an inverse dependence on crosslink density, the hydrogel swells. Thus, as with the GOX-based hydrogels, free glucose concentration variations can be detected by measuring filament length changes in the GSF. FIG. 4 shows an example of GSF elongation in the presence of free glucose due to competitive binding to the immobilized GBM between the free glucose and the covalently bound diols in PVA in the GSF.

Synthesis of Boronic Acid-Containing Complex Gels

A boronic acid group in a tetrahedral anionic form makes covalent complexes with diol compounds including PVA and glucose. Due to this unique characteristic of a boronic acid group, it can be incorporated into a polymer backbone as a GBM. The hydroxyl groups of PVA in complexes with a boronic acid group of the polymer backbone can substitute with glucose hydroxyl groups. Such a competitive binding between glucose and hydroxyl groups of PVA against boronic acid moieties induces a change in the crosslinking density, thus, the complex hydrogels can swell or de-swell in response to the concentration of glucose. Basic tertiary amino groups in a polymer backbone contribute to the formation of the stable complexes of boronic acid and diol compounds (PVA and glucose) at the physiological pH in aqueous solutions. A boronic acid based hydrogel may be prepared with N-[3-(N,N'-dimethylamino)propyl] acrylamide (DMAPAA) and 3-methacrylamidophenylboronic acid (MAAPBA) as described previous investigators.

To prepare MAAPBA, 0.1 M of 3-aminophenylboronic acid hemisulfate is preferably dissolved in 100 ml of deionized water and stirred with a magnetic stirring bar. The pH of the solution is preferably adjusted to pH 4.8 by the addition of NaOH solution and cooled to 4° C. in an ice bath. After cooling, 0.1 M of 1-[3(dimethylamino)propyl]3-ethylcarbodiimide hydrochloride and 0.1 M of acrylic acid is preferably added to the solution and then the pH of the solution is preferably again adjusted to pH 4.8. After one hour of stirring, MAAPBA is preferably extracted with diethyl ether and after the removal of diethyl ether by evaporation, MAAPBA is preferably recrystallized from water.

To synthesize a boronic acid-containing copolymer, poly (DMAA-co-MAAPBA-co-DMAPAA-co-BMA) copolymer is preferably synthesized by radical copolymerization in ethanol. MAAPBA, N,N-dimethylacrylamide (DMAA), isobutylmethacrylate (BMA), DMAPAA, and ethanol is preferably put together into a 50 ml glass flask. The solution is preferably stirred with a magnetic stirring bar and bubbled with nitrogen gas for 20 min. Ammonium persulfate (APS) is preferably used as an initiator. After adding APS to the solution the copolymerization reaction is preferably carried out for 3 hours at 70° C. under nitrogen gas atmosphere with stirring. The product copolymer is preferably precipitated with diethyl ether and dried in vacuum.

To form a complexation of boronic acid-containing copolymer and PVA, 2 wt % boronic acid-containing copolymer dissolved in methanol and 2 wt % PVA solution in dimethyl sulfoxide (DMSO) is preferably mixed to form complexes between hydroxyl groups of PVA and boronic acid group. The complex polymer solution then inject between glass plates with the gap set using a Teflon spacer (0.2 mm). After drying at 45° C. for 20 h, the complex gel slab is preferably separated from the two glass plates with a razor blade and cut into a 0.5 mm by 10 mm filament using a cutter.

Synthesis of a Series of GSF Based on a Competitive Binding Mechanism with Non-Covalent Bond This new type of GSF contains immobilized glucose binding molecules (GBM) and immobilized glucose moieties, with other pendant groups as necessary to achieve the desired sensitivity, response, and durability. The GBM are preferably be a lectin like Con A, glucokinase, xylose isomerase, and isolactin I. The volume of this hydrogel responds to the environmental concentration of free glucose via a competitive binding mechanism that is very specific and does not require oxygen or enzymes. When immobilized GBM reversibly binds to immobilized glucose moieties, it creates crosslinks in the hydrogel that act to resist hydrogel swelling. As shown in FIG. 5, when the concentration of glucose in the solution surrounding the hydrogel increases, free glucose diffuses into the gel and displaces immobilized glucose moieties from the binding sites of the GBM, thereby decreasing the density of crosslinks in the hydrogel. Since hydrogel volume has an inverse dependence on crosslink density, the hydrogel swells. Thus, as with the GOX-based hydrogels, free glucose concentration variations can be detected by measuring filament length changes in the chip.

The competition hydrogel contains both GBM and hexose saccharides chemically or physically immobilized on the hydrogel backbone. FIG. 5 shows an example of GSF elongation in the presence of free glucose due to competitive binding to the immobilized GBM between the free glucose and the chemically bound glucose in the hydrogel.

Immobilization of Glucose and Con A to Polymer Backbone

Several glucose-conjugated and GBM-conjugated vinyl monomers are preferably synthesized as described below.

These conjugated monomers are then co-polymerized with crosslinkers and either cationic or anionic monomers. The crosslinker introduces a small number of permanent crosslinks into the hydrogel in order to keep hydrogel integrity at all free glucose concentrations.

For binding of a conjugated hexose to Con A with high affinity, a minimal configurational structure with unmodified hydroxyl groups on the C-3, C-4, and C-6 position is essential. The binding affinity of a hexose saccharide to Con A is dependent upon the configurational factor at C-2 hydroxyl group, since mannose with the axial position at C-2 hydroxyl group has 40 times higher binding affinity for Con A than mannose with the equatorial position at C-2 hydroxyl group. As an example, a vinyl group is preferably attached at the C-1 position, forming allyl glucose (AG) through an etherification reaction of glucose with allyl alcohol (FIG. 6).

Figure 7:
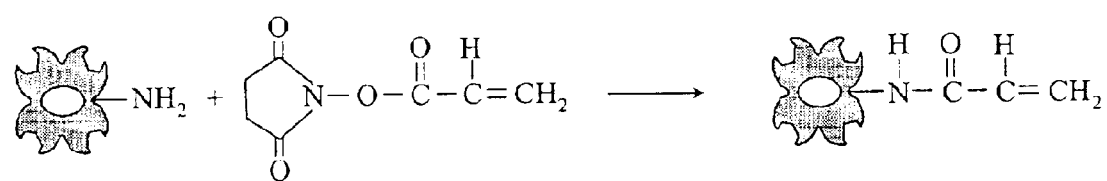
FIG. 7 is a schematic diagram for the conjugation of a vinyl group to Con A with N-acryloxysuccinimide.

Con A is preferably chemically and physically immobilized into the hydrogel network following a procedure described in previous studies. Vinyl groups are preferably conjugated to Con A as shown in FIG. 7. The conjugated Con A is preferably purified using dialysis or ultrafiltration with a membrane (molecular weight cutoff of 10,000 KDa). The concentrations of conjugated vinyl groups on Con A are preferably determined by spectrophotometry, and the purified Con A concentrated using a speed vacuum drier. Con A is preferably chemically incorporated into the hydrogel network via the vinyl groups.

N-(2,2)-dimethylaminoethyl methacrlate (DMA), HPMA, acrylamide (AM), sodium acrylate (NaAA), MBA, ammonium persulfate (APS), N, N, N', N'-tetramethylethylenediamine, and the vinyl conjugates are preferably used to synthesize the GSF. The amount of conjugated Con A and conjugated glucose are preferably varied between 0.1 mM to 10 mM to find a GSF with optimal response to glucose concentrations of 50 mg/dL (0.03 mM) to 1000 mg/dL (6.3 mM). The backbone of the polymer is preferably composed of neutral monomers such as AM and HPMA and/or charged monomers such as NaAA and DMA. Density of the charged pendant groups is preferably varied to adjust the swelling ratio of the GSF.

The reaction ratio of AG to Con A, monomer, and cross-linking agents is preferably optimized to achieve the greatest response of hydrogel filament length to change in glucose concentration. Alternatively, p-nitrophenyl-α-D-mannopyranoside, p-nitrophenyl-α-D-glucopyranoside, glucosyloxyethyl methacrylate (GEMA), N-glucosylacrylamide (NGAM), and disaccharide-based monomers containing a glucose moiety preferably used instead of glucose for immobilization on the polymer. Also, other GBM such as glucokinase, xylose isomerase, and isolactin I are preferably immobilized on the polymer chemically or physically instead of Con A.

Glucose Binding Molecules and other Analyte Binding Molecules

TABLE 2 contains a list of glucose and glucose binding partners to which the method and biosensor of the invention can be applied. The glucose binding partner molecule should bind the glucose with sufficiently high specificity. For examples, an antibody (ABM) tightly binds with an antigen (glucose) with a high specificity.

TABLE 2

| Analyte Binding Molecule (ABM) | Glucose |
| --- | --- |
| Antibody | Antigen |
| Enzyme and Kinase | Cofactor, Substrate, and Inhibitor |

TABLE 2-continued

| Analyte Binding Molecule (ABM) | Glucose |
| --- | --- |
| Protein A | IGG |
| Concanavalin A | D-Sugar |
| Lectins | Carbohyrates |
| Boronic acid | 1,2-cis-Diol sugars |
| Thiol | Cystein |
| Receptors (Cell membrane receptors, Cytosol receptors, and Nuclear receptors) | Growth factors, Hormones, Metal ions, Modifed molecules such as phospholated. |
| Heparin, DNA, and RNA | Protamine, Polylysine, Polyarginine |
| Poly U, Poly A, Poly Lysine, and Poly Arginine | Nucleic acid |
| Triazine dye | Nucleotide |
| Commassie blue and Azure A | Arginine, Lysine, and Proteins |
| Metal binding molecules including chelating agents | Ca ion, Mg ion, etc |

Semipermeable Membrane

The semipermeable membranes used in the biosensor of the invention, such as membrane 12, FIG. 1, are preferably made of a material rigid enough to substantially constrain the GSF to one-dimensional expansion or contraction. The semipermeable membrane is permeable to the passage of glucose, oxygen, and gluconic acid. However, it is totally impermeable to the passage of blood clots, cells, and proteins.

The semipermeable membrane is preferably an inert, nontoxic material that maintains its integrity when implanted in humans. A suitable biocompatible semipermeable material, to minimize immune reactions and to prevent protein and cell absorption, is preferably selected from the following groups of polymers: cellulose acetate, methyl cellulose, polyvinyl alcohol, polypropylene, HEMA, tetraacrylated poly(ethylene glycol) (PEG), and/or polyurethane. Cross-linked aliphatic polyurethanes are preferably synthesize in order to enhance biocompatibility and to retard biodegradation due to its controllable permeability.

The porosity of the polyurethane membrane affects both immunoprotection and the selective permeation of molecules. Membrane thickness is also important for immunoprotection, as well as for diffusion of glucose and oxygen. The maximal pore volume fraction and the minimum possible thickness are important to achieve rapid diffusion of glucose and oxygen through the semipermeable membrane. Also, the pore volume fraction, the average pore diameter, and wall thickness affect the mechanical strength of the membrane. Different porosities and thickness (0.01 mm to 0.5 mm) are formed to find the optimal membrane. The pore size is preferably controlled between 0.1 micrometer to 15 micrometer by varying the crystal size of the salt particles dispersed in the polyurethane solution before crosslinking. Preferably, different sizes of salt particles such as sodium fluoride and zinc hydroxide are used at various concentrations. Different concentrations of linoleic acid, heparin and/or PEG are preferably incorporated in the polyurethane in order to increase the crosslinking efficiency and biocompatibility. The crosslinker dicumyl peroxide is preferably purified several times and used in the polyurethane network. The salt crystals imbedded in the polyurethane film is preferably leached out by submerging the film in water with sodium fluoride, acetic buffer, or in EDTA solution. This creates the porosity. Next the membrane is preferably dried for more than 2 days at room temperature. The polyurethane is preferably coated or bonded over the GSF.

Hydrogel Displacement Measurement using pH-Sensitive Hydrogel

Figure 8A:
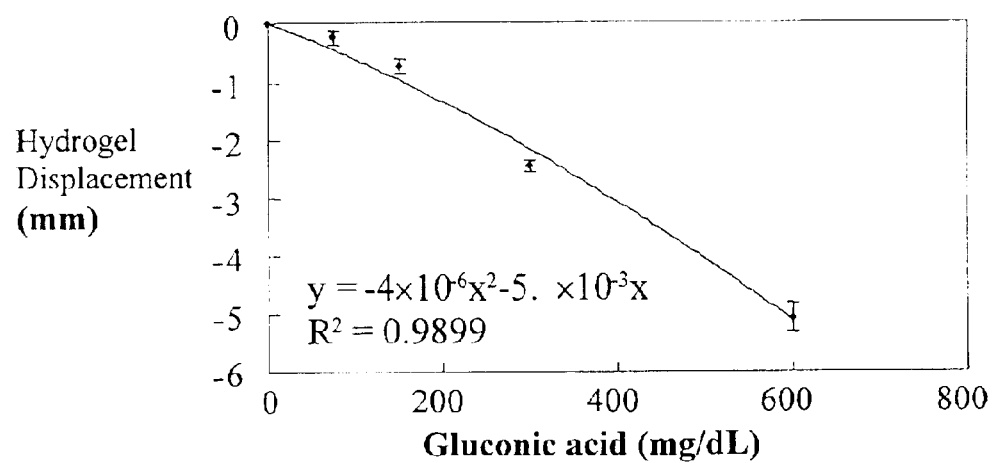
FIG. 8A depicts graphically changes in hydrogel displacement length for an acidic pH-sensitive hydrogel for different acid concentrations.
Figure 8B:
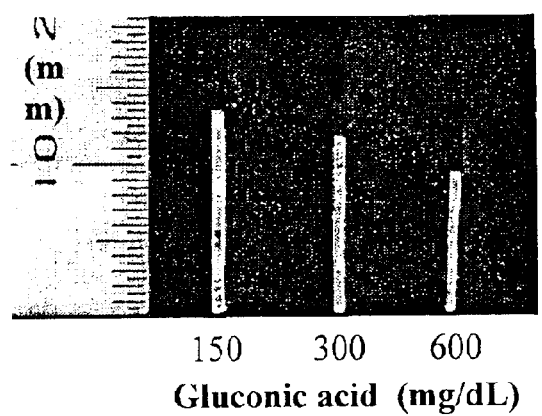
FIG. 8B depicts a scanned image of a hydrogel at different displacement lengths.

FIGS. 8A and 8B depict the measurement of displacement volume changes for a test system using a pH-sensitive hydrogel subjected to varying concentrations of gluconic acid. The hydrogel was composed of AM, MBA, and NaAA. Slices of hydrogel (0.5 mm width, 0.4 mm thickness and 13.97 mm length) were immersed in citric buffer (ionic strength, [I]=0.15) containing different gluconic acid concentrations (0, 75, 150, 300, and 600 mg/dL), after 30 minutes changes in hydrogel length were measured using a ruler (Mitutoyo calipers). A plot of the displacement vs. gluconic acid concentration is depicted in FIG. 8A, while FIG. 8B represents a computer-scanned picture of the hydrogel slice, showing the change in hydrogel length with gluconic acid concentration. FIG. 8A shows hydrogel displacement in millimeter for an acidic pH-sensitive hydrogel as a function of gluconic acid concentration. The hydrogel is composed of acrylamide/sodium acrylate/N, N'-methylene-bis-acrylamide (MBA), mole ratio 50:50:2. Hydrogel displacement is defined as hydrogel gel length at concentration X minus hydrogel length at a reference condition. Negative displacement represents hydrogel contraction; positive displacement represents hydrogel expansion. In the experiment of results shown in FIG. 8A, the hydrogel displacement increases with increasing gluconic acid concentration, which corresponds to a decrease in pH within the hydrogel. From 0 to 600 mg/dL, the displacement is 5.09 mm, which is a contraction of about 36% compared to the reference solution. FIG. 8B shows a hydrogel scan image produced with an EPSON perfection 636U scanner, for hydrogels in different gluconic acid concentrations.

The pH sensitivity of hydrogel displacement can also be controlled by varying the elements of the polymer composition, such as the pKa of ionizable pendant groups, the amount of ionizable pendant group, crosslinking density, crosslinker type, and hydrophobicity of the polymer backbone.

The glucose-dependent elongation of the GSF on the GSF can be predicted by measuring the swelling ratio of the unconfined GSF synthesized in solutions of varying concentration of free glucose. The elongation ratios are preferably proportional to the free glucose concentration. Slices of GSF are preferably immersed in a PBS buffer or serum with different amounts of glucose (50–450 mg/dL), and the changes in GSF length and mass are preferably monitored.

Electric Design of the Photometric Hydrogel Biosensor

Figure 9:
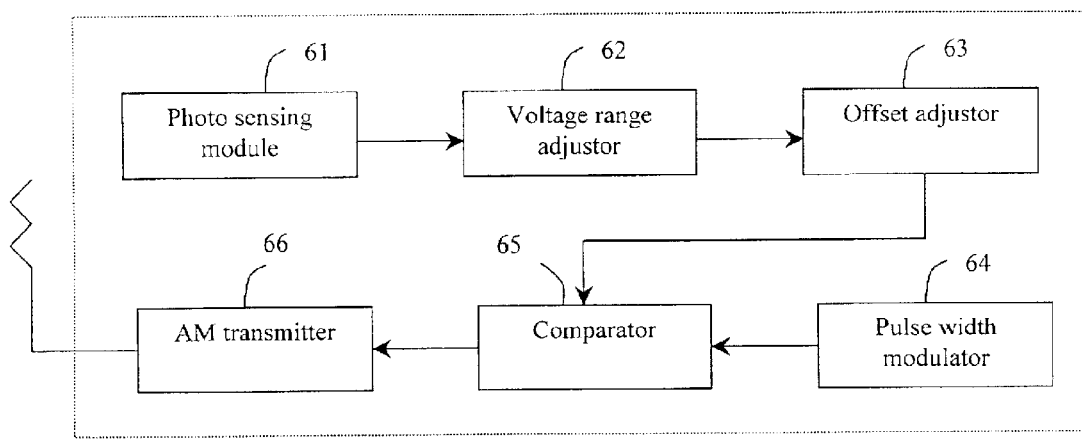
FIG. 9 is a block diagram of an embodiment of a wireless photometric sensor of the invention.
Figure 10:
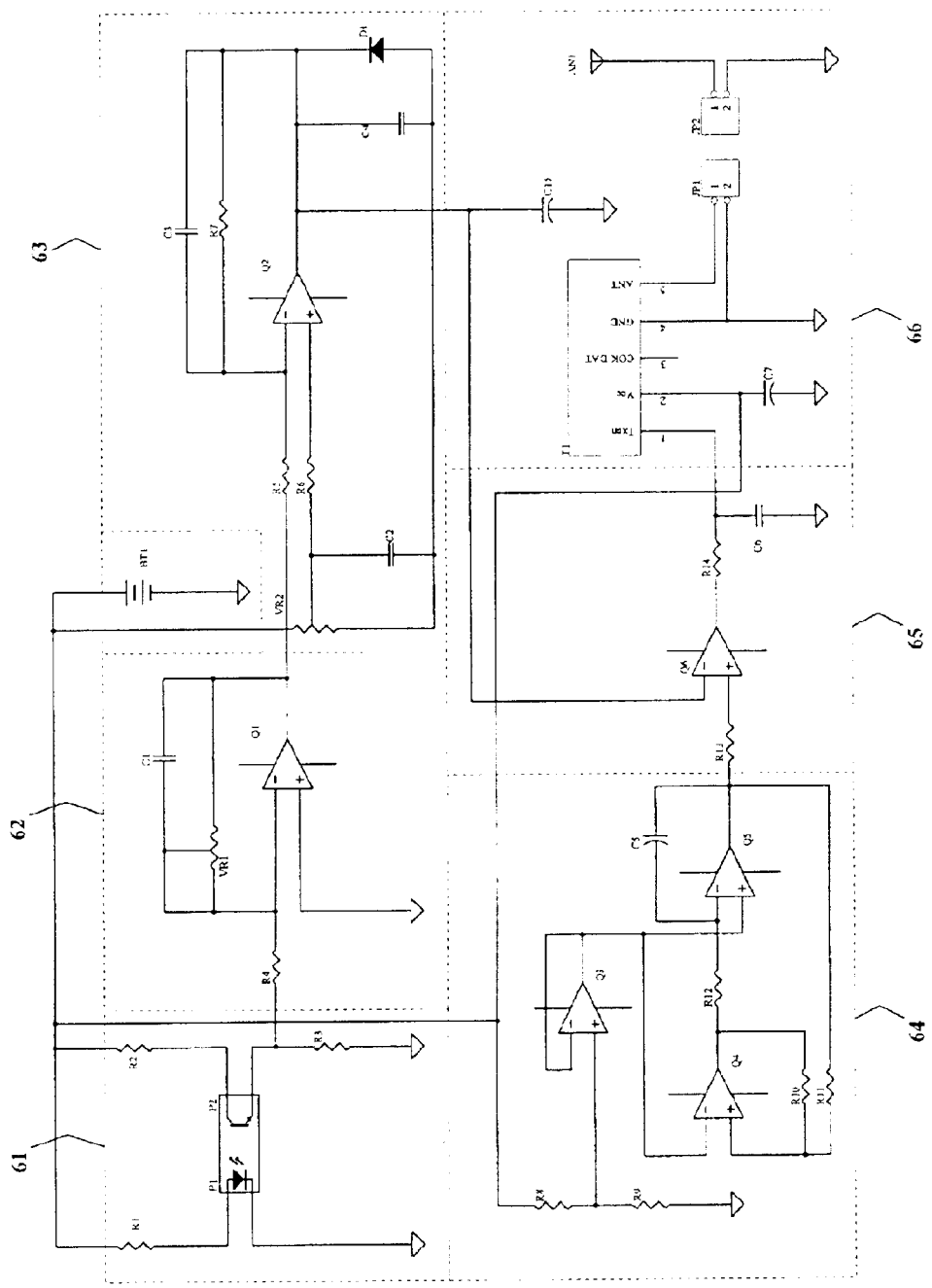
FIG. 10 is a circuit diagram of a wireless photometric sensor implementing the block diagram of FIG. 9.

FIG. 9 shows a block diagram of electronic circuitry for a wireless photometric glucose measurement system, and FIG. 10 shows one circuit embodiment of that block diagram. The photometric glucose biosensor obtains power from a battery BT1 in FIG. 10 and not shown in FIG. 9, but located inside the biosensor. The biosensor transmits the electric signal reflective of the measured light intensity with a wireless means such as the AM transmitter of FIG. 9. The photo diode P1, FIG. 10, may be a SIM22ST from ROHM or a SPI5842 from AUK, and emits an infrared light with a peak wavelength of 800 nm to 850 nm. The phototransistor P2 may be a RPM20PB, RPM22PB, or RPM25PT from ROHM and filters out visible light, preferably less than 750 nm, and produce electric current depending on the intensity of incoming infrared light. The measured signal from the phototransistor P2 is conditioned in voltage range adjustor 62 in order to fit into the offset compensation circuit 63 for offset removal. The conditioned voltage signal is then prepared for AM wireless transmission by AM transmitter 66 by using pulse width modulator 64 and comparator 65, which generate the corresponding frequency depending on the level of the conditioned voltage. Any wireless data transmission device or method may be used to transmit the signal such as those using a Bluetooth protocol. Operation of the circuitry shown will be obvious to those skilled in the art, so will not be described in further detail.

Figure 11:
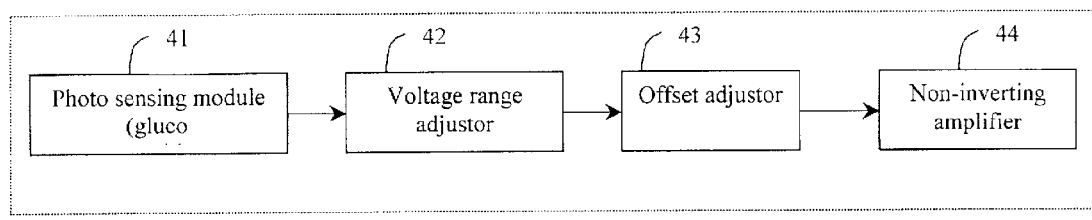
FIG. 11 is a block diagram of another embodiment of a photometric sensor of the invention.
Figure 12:
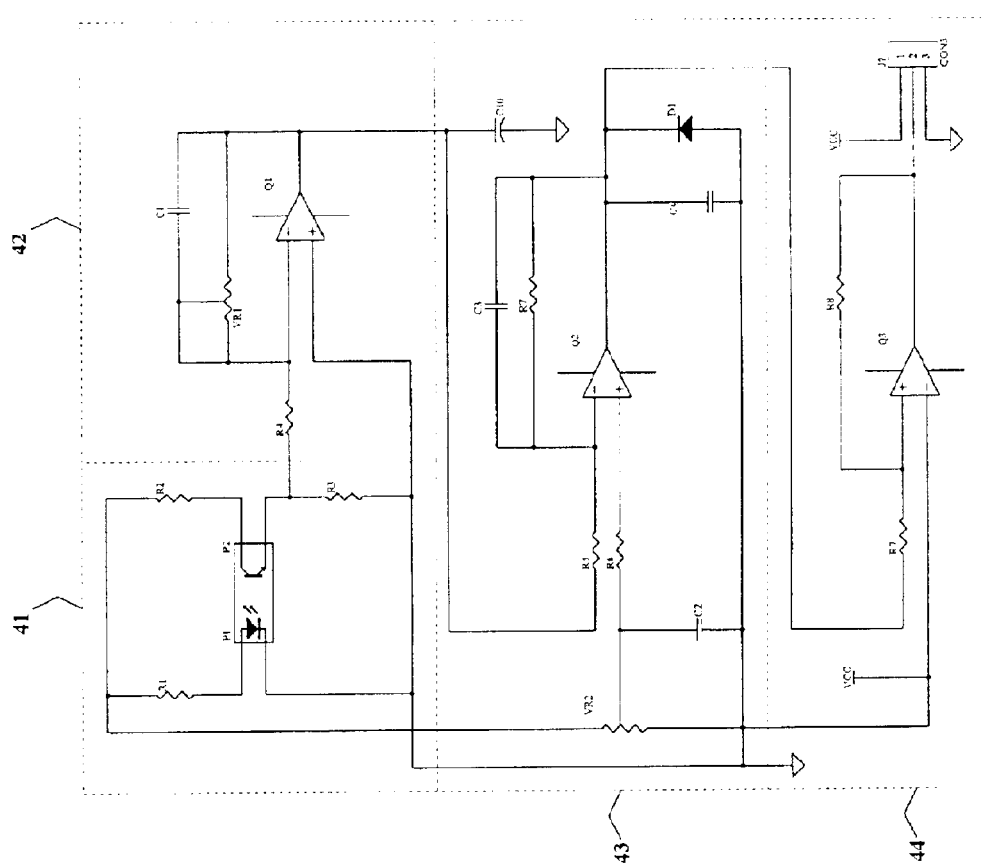
FIG. 12 is a circuit diagram of a photometric sensor implementing the block diagram of FIG. 11.

FIG. 11 shows a block diagram of electronic circuitry for a non-wireless photometric glucose measurement system, and FIG. 12 shows one circuit embodiment of that block diagram. The photometric sensing module 41 consists of photo diode P1, FIG. 12, and phototransistor P2, which are powered by an outside device such as a health monitoring system, not shown. Voltage range adjustor 42 and offset compensation circuit 43 play the same role as those of the wireless sensor in FIG. 13. A non-inverting amplifier 44 such as a JRC2901 from JRC amplifies the compensated voltage before transferring it to the health monitoring system in order to have a better noise protection.

Compensation with Reference Hydrogel

Figure 13:
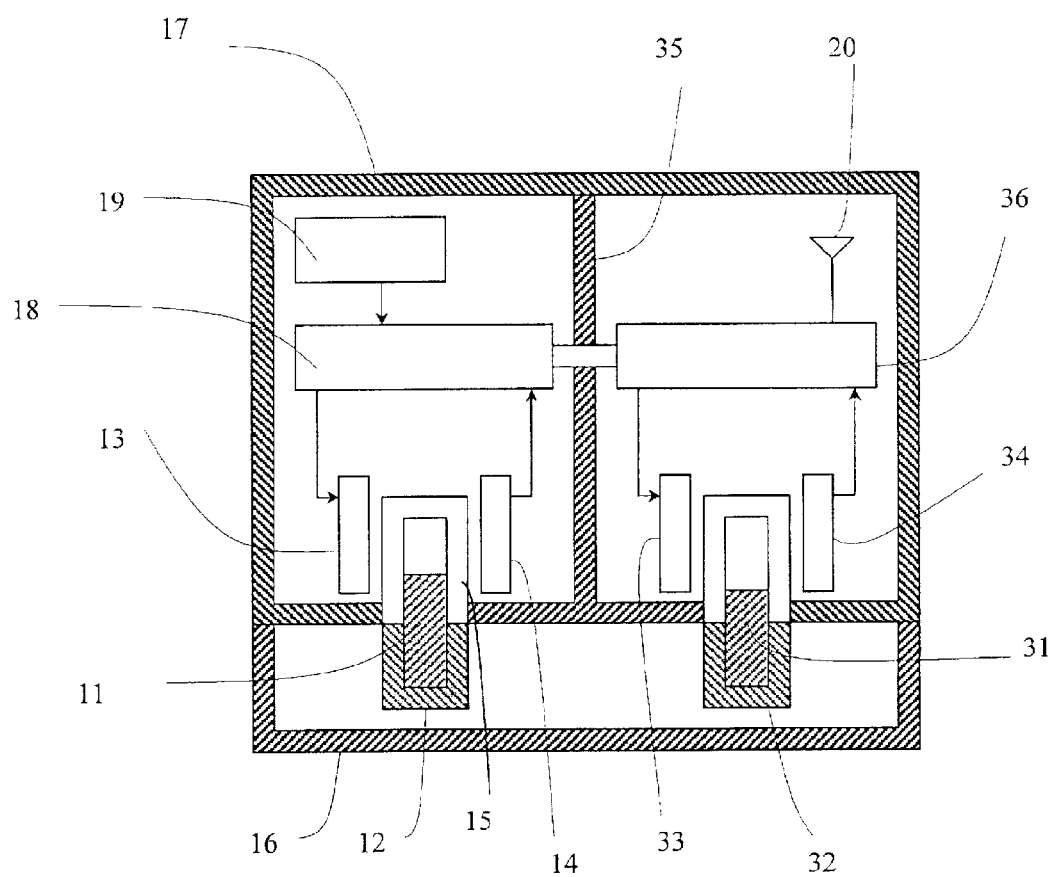
FIG. 13 shows schematically a design of photometric glucose biosensor similar to that of FIG. 1, but with a reference hydrogel.

The GSF is preferably designed to respond only to glucose. However, in the case that the GSF reacts to some substance other than glucose, the non-specific swelling can be compensated for by examining a reference hydrogel filament 31, FIG. 13, that is also placed in the photometric biosensor. The reference hydrogel is preferably synthesized of the same monomers and co-monomers, and crosslinkers as used for the GSF without GBM or other enzymes such as GOX. A design for a biosensor including a reference hydrogel filament 31 is shown in FIG. 13. The original length of the reference hydrogel filament 31 is known from the fabrication of the photometric biosensor. When the reference hydrogel filament swells or contract from its original length, the deviation, if any, is preferably either added to or subtracted from the swelling displacement of the GSF 12. Another set of a photo diode 33 and a phototransistor 34 is engaged to measure the displacement change of the reference hydrogel 31 that is contained in the semi-permeable column 32. The deviation, if any, is detected and processed in the circuit 36 for compensation. It is preferable that a divider 35 should divide the compensating part of the biosensor in order to avoid light interference from the other part of the biosensor.

Figure 14:
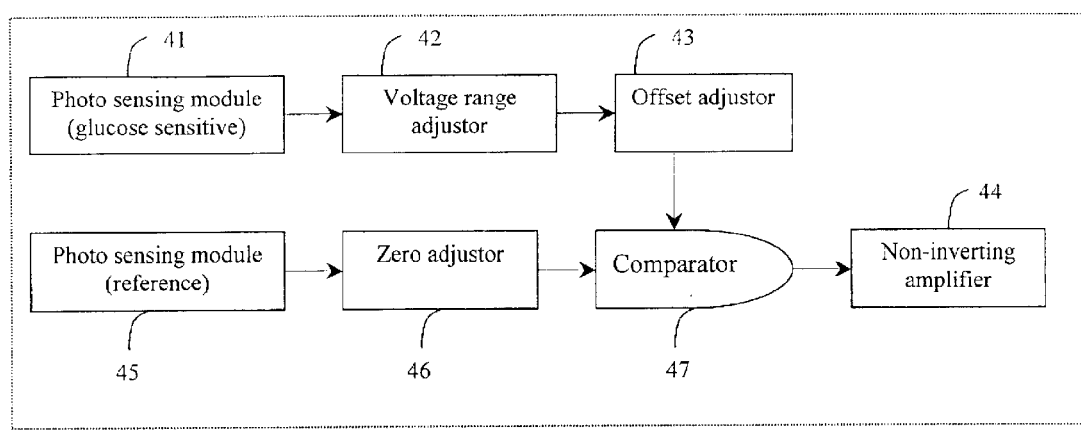
FIG. 14 is a block diagram of a photometric glucose biosensor with a reference hydrogel such as shown in FIG. 13.

FIG. 14 shows a block diagram of electronic circuitry for a biosensor with a reference hydrogel. The photo-sensing module 45 for the reference hydrogel filament and its supporting circuit should be designed to give a compensation signal only if the reference changes from its original length, in order to compensate the non-specific swelling of the GSF. The zero adjustor 46 sets the compensating output voltage to zero when the reference remains its original length. If the original length of the reference changes, the compensating output voltage changes from zero to a certain voltage level depending on the reference hydrogel displacement, and the compensating voltage is added to or subtracted from the measured voltage level due to GSF by using comparator 47 such as a LM391 or a 2901.

Alternative Design of Photometric Displacement Measurement Device

Figure 15:
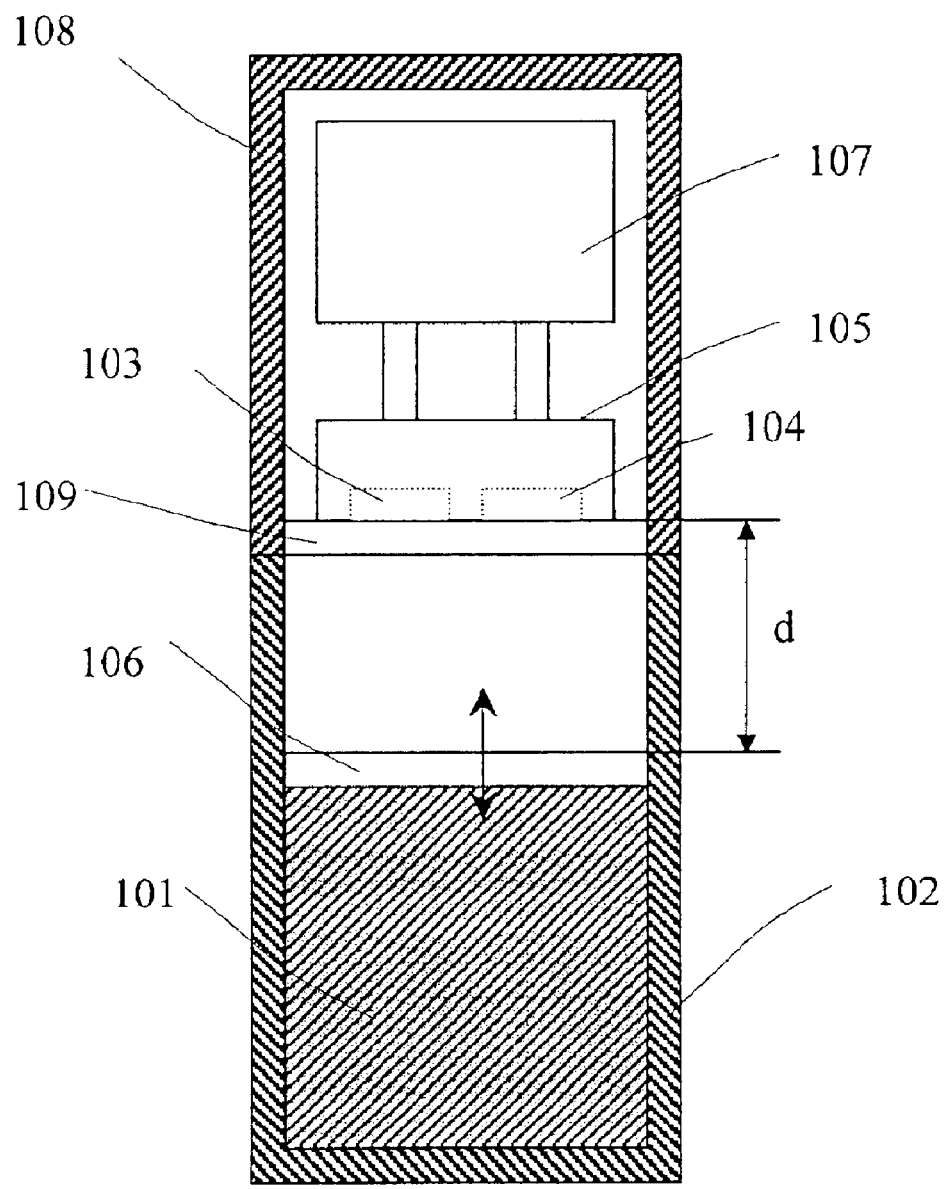
FIG. 15 shows schematically a design of photo reflective biosensor.

FIG. 15 shows an alternative embodiment of a photometric glucose biosensor. The photo diode 103 and phototransistor 104 are placed at the end of the hydrogel filament 101. The photo diode 103 emits infrared light and the phototransistor 104 detects the incoming infrared light reflected to it from the hydrogel. Infrared light from the photo diode 103 travels until it hits the reflecting end of the hydrogel 101 and reflects back to the phototransistor 104. A reflecting material 106, such as reflecting metal disc, may be positioned on the end of the hydrogel filament 101 to provide better light reflection. The intensity of the incoming light to the phototransistor varies according to the distance d of the reflecting material 106 from the photo diode and phototransistor. By the amount of the reflected light intensity, a corresponding electric current is generated from the phototransistor, and the electric current is processed to report a data signal reflective of light intensity and which is also indicative of the glucose level in the same manner as for the previous photometric system of FIG. 1. A transparent material 109 preferably separates the hydrogel 101 from the photo diode 103 and phototransistor 104.

The glucose-sensitive hydrogel 101 is contained in a semi-permeable column 102 so that body fluid comes in and out easily and the GSF swells according to glucose concentration level in the body fluid. The filament is fixed to the column at one end and the reflective material 106 is attached to the other end of the filament. The reflective material 106 reflects the incoming infrared light from the photo diode 103 to the phototransistor 104. The hydrogel filament itself can be dyed or coated with a reflective material so that it reflects the incoming light without an additional reflector. The electric components including circuitry 107, photo diode 103, and phototransistor 104 are enclosed within a non-permeable container 108 to protect them from body fluid. The circuitry of FIG. 10 or FIG. 12 can be used. The non-permeable transparent divider 109 is used to protect the electronic components against fluid and to allow the infrared light from photo diode 103 and the reflected light directed to phototransistor 104 to pass through, and is attached to the face of the photo diode and phototransistor. The devices of photo diode 103 and phototransistor 104 for the reflective light intensity measurement may be fabricated as one device that is called a photoreflector 105. Photoreflectors such as RPR-220 and RPR-359F from ROHM, which have a photo diode and a phototransistor in one device, may be used.

Figure 16:
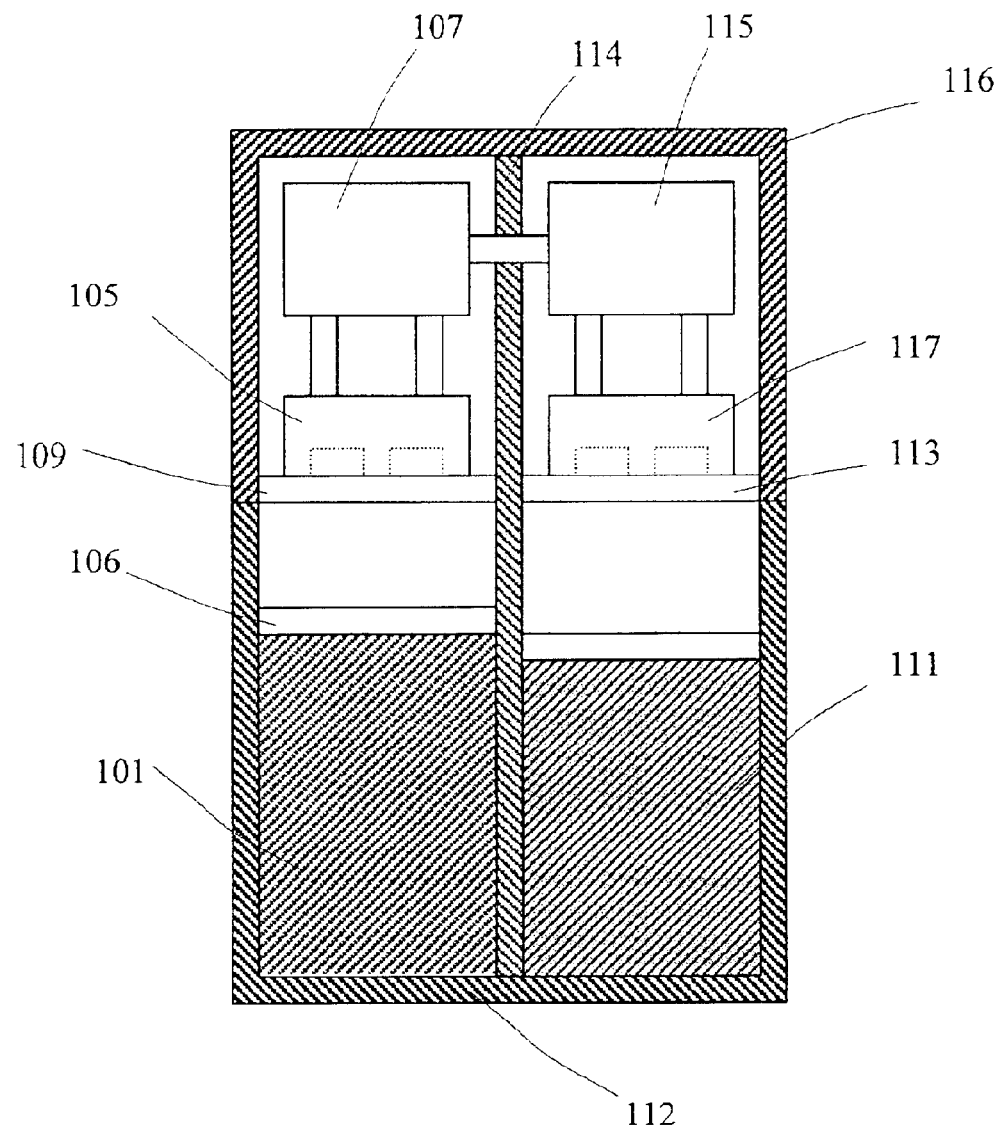
FIG. 16 shows schematically a design of a photo reflective glucose biosensor similar to that of FIG. 15, but with a reference hydrogel.

FIG. 16 shows another example for the photo reflective displacement measurement system with a reference hydrogel filament 111, which is intended to compensate for any non-specific hydrogel response. The GSF 101 swells, but the reference hydrogel filament 111 preferably remains an original length unless a variation due to non-specific response occurs. The reference hydrogel is laid in a semi-permeable column 112 and is exposed to a photoreflector 117 having a photo diode and a phototransistor to detect the variation of the reference hydrogel 111 from the original length. The compensating part of the biosensor is preferably divided by a divider 114 to avoid light interference from each other. The circuit for the compensation 115 is enclosed with a rigid non-permeable material 116.

Glucose Concentration Determination and Display

If it is desired to determine the glucose level for display or other purpose, the data signal reflective of the light intensity, which is also indicative of the glucose level, may be converted to an output signal representing the glucose level in the fluid being tested or monitored. This may be done in a computing means such as computing circuitry or a microprocessor or other computer which compares the data signal reported to a calibration curve, such as may be in the form of a calibration table in the computer. The calibration curve indicates the glucose level which corresponds to the data signal (light intensity signal) reported. This glucose level may then be displayed in a manner having meaning to a person seeing the display. The calibration curve will usually be generated by determining the data signal produced by the biosensor for a number of standard solutions of known glucose concentration spanning the range of expected glucose levels to be measured by the biosensor.

A similar procedure would be used to determine concentration levels of analytes other than glucose.

Operation Principles of the Health Alarm System

Figure 17:
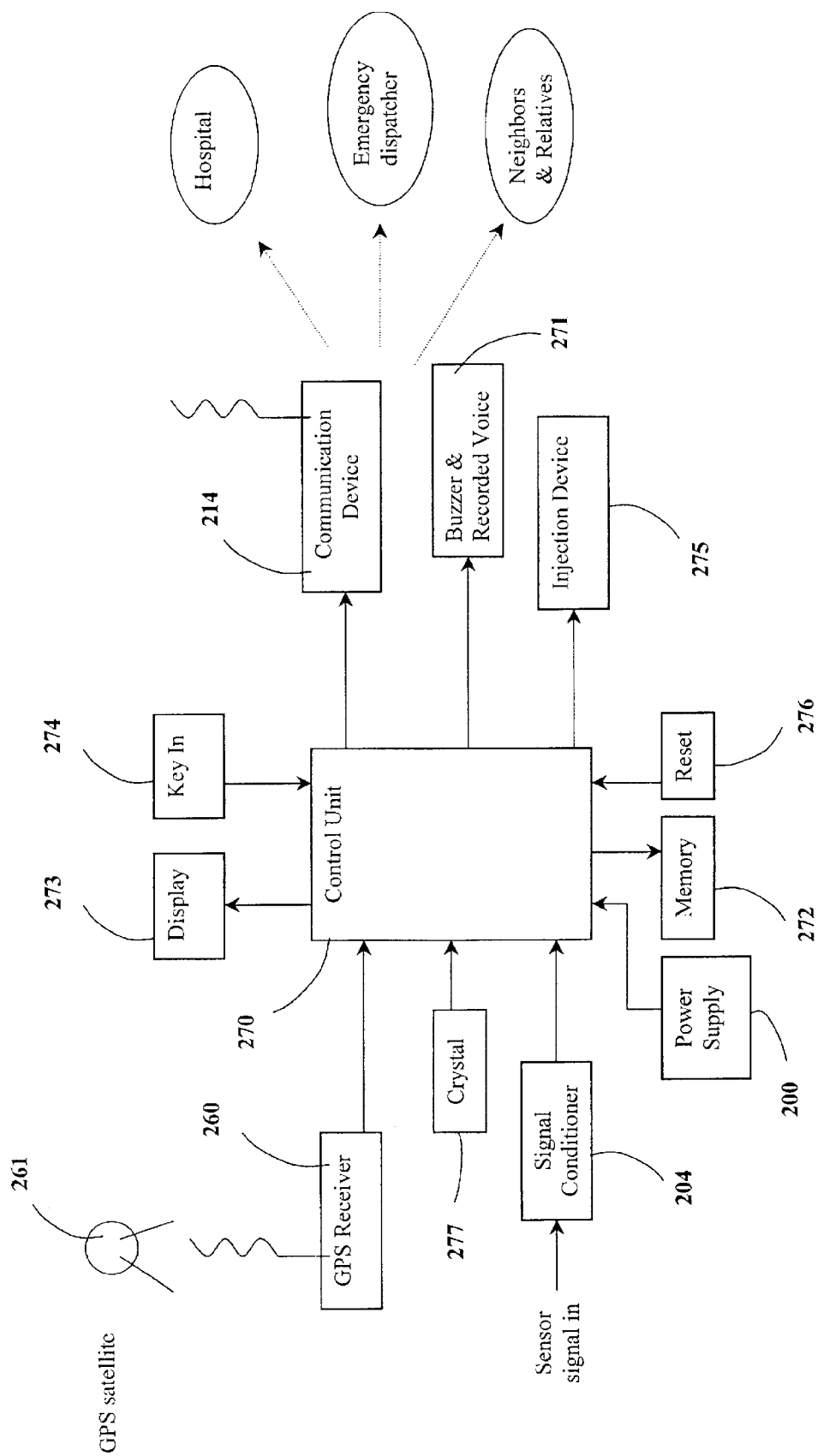
FIG. 17 is a block diagram of a preferred embodiment of an automatic health alarm system.

The output of a photometric sensor as described is preferably transferred by wire or wireless transmission to the health alarm system, as the "sensor signal in", FIG. 17, and is monitored and compared with a preset value (or threshold value). If the sensor output is out of the preset range, an alarm signal is preferably generated. This alarm signal can be further utilized to actuate a certain alarm protocol such as automatic dialing and sending of a prerecorded message corresponding to the condition detected.

A preferred embodiment of the automatic alarm system is depicted in FIG. 17, and circuits useful in this embodiment are shown in FIGS. 18–25. As seen in FIG. 17, the major elements are a power supply 200, a signal conditioning unit 204, a global positioning system (GPS) receiver 260, a MCU circuit unit 270, and a data transmitter 214.

Figure 18:
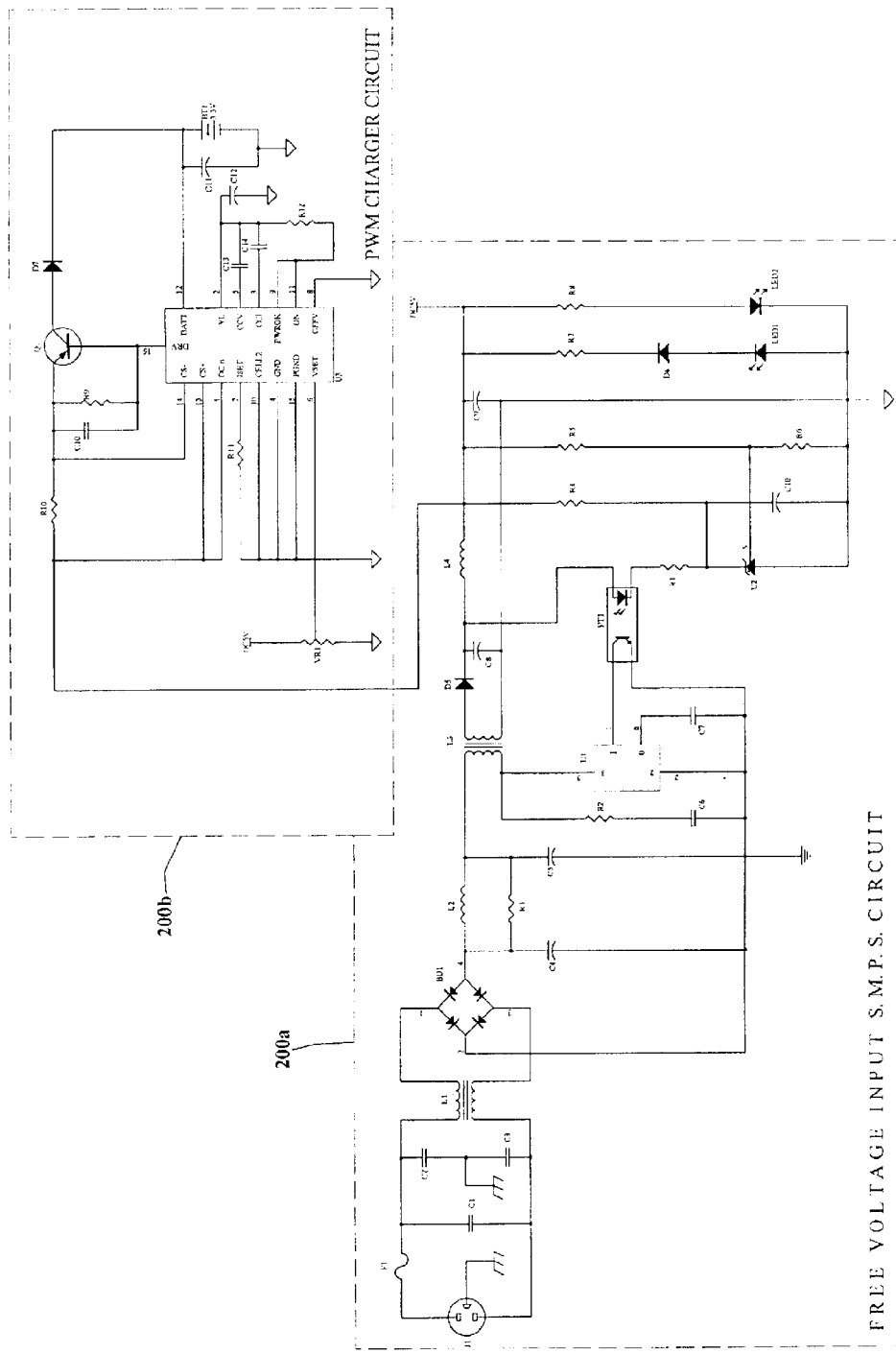
FIG. 18 is a power supply circuit for the alarm system embodiment of FIG. 17

The power supply 200 preferably provides electric energy to all the elements of the device requiring power. Considering portability of the device, a battery is the preferred choice for supplying power. The particular battery used will be chosen based upon power requirements of all the circuit elements. A +3.3-volt (+3.3 V) rechargeable battery and a charging system have been found satisfactory for the circuitry of FIGS. 17–25. For a battery charger, SMPS (Switching Mode Power Supply) 200a in FIG. 18 is preferably used to convert an AC input voltage of free range about AC 85 V to AC 265 V into constant DC voltage of +5 V. By using of the output DC voltage from SMPS, charging circuit 200b charges the rechargeable battery according to the battery capacity and remaining battery level. In this charging system, Li-ion, Ni-ca, and Ni-H are preferably used for the rechargeable battery 200c in FIG. 21. A low battery indicator and a charging status indicator should be an essential part of the charging system. The rechargeable battery can be charged up to +3.3 V, which is supplied to the circuit as a whole except the LCD and the transmitter and micro controller unit (MCU). Additional +5 V is needed to operate LCD and transmitter, and this voltage is preferably acquired from the battery by using of a conventional DC-DC converter 200d in FIG. 21.

The need for the signal conditioning unit 204 in FIG. 17 depends on the quality of the signal from a sensor. If the sensor signal comes along with a great deal of environmental noise and/or a low voltage input, the signal conditioning circuit 204 is preferably necessary to operate the device in a reliable manner. A signal-conditioning unit 204 is preferably designed for a noise reduction and amplification for an input signal from a sensor. A prepackaged multi-step amplification circuit, the so-called "instrumentation amplifier" is commercially available. However, for a prototype device, a chopper-op amp IC (e.g. MAX 420 or MAX421 from Maxim) and/or a quad-op amp IC (e.g., LM 384 from National Semiconductors) preferably serve well by providing multiple amplifiers for amplification of a low voltage signal without noise. A differential amplifier is excellent in removing common mode noise. A low-pass filter after differential amplification preferably further decrease high frequency noise. An RC time constant of 0.1 to 1 seconds is preferably appropriate. For example, an RC time constant of 1 second can be obtained using 100 kohm and 10 mF.

Figure 19:
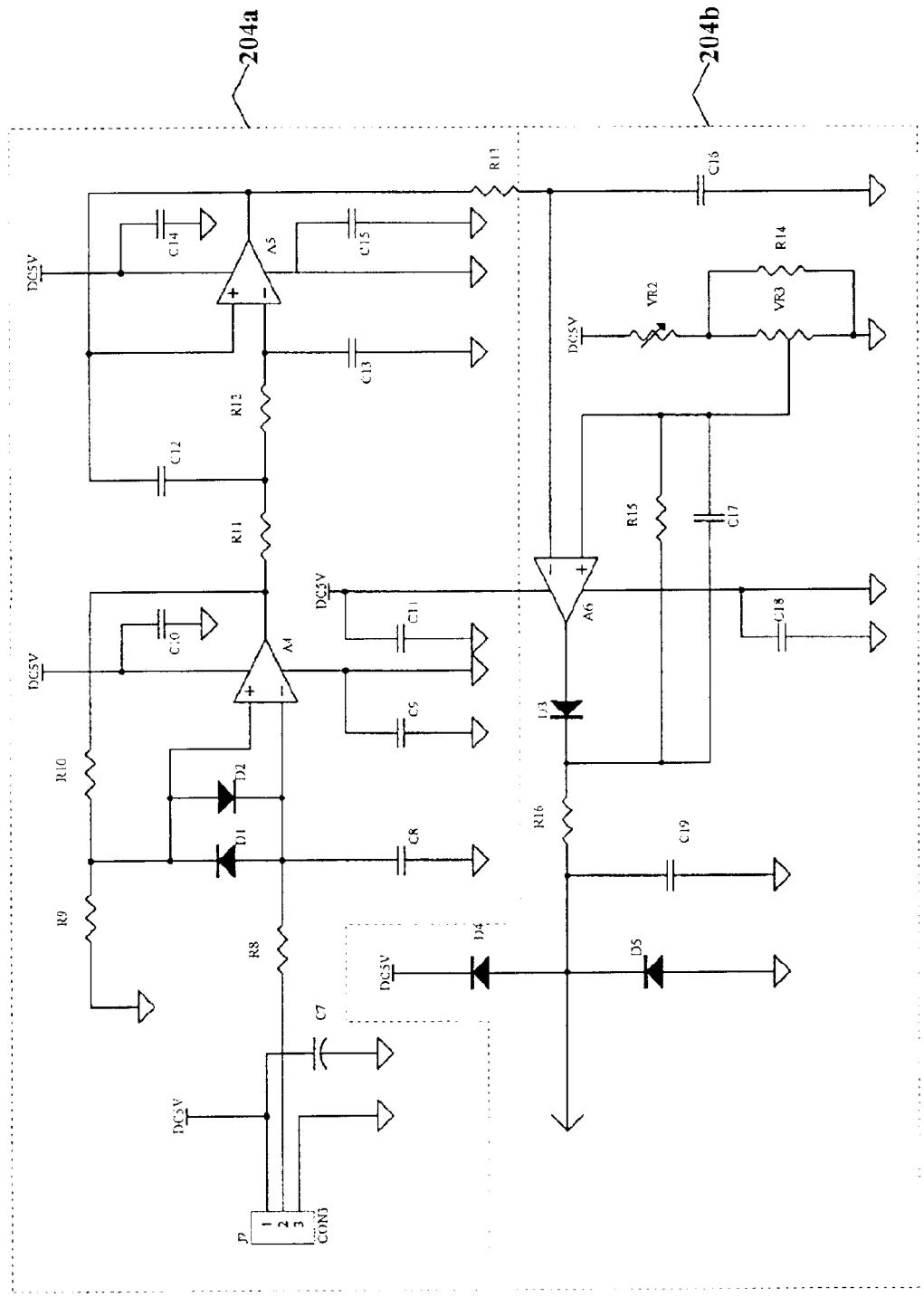
FIG. 19 depicts a signal conditioning circuit for the alarm system of FIG. 17.
Figure 20:
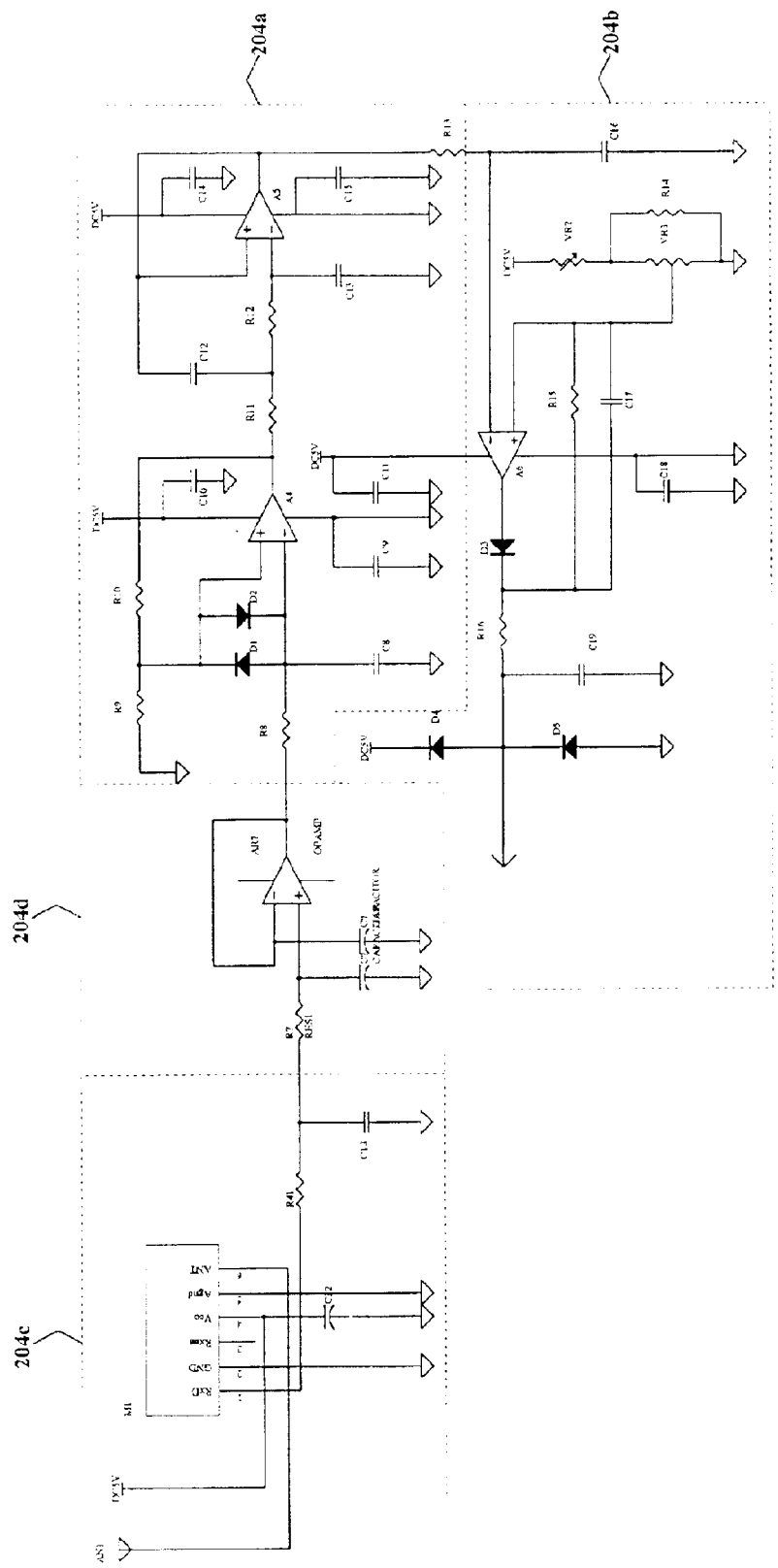
FIG. 20 depicts a signal conditioning circuit for the alarm system of FIG. 17.

Chopper-stabilized amp ICs (A4, A5, and A6) in FIG. 19 are preferably used for a prototype device in signal conditioning circuit. The op-amps are a monolithic chopper op-amp having precise input characteristics. The amplification circuit 204a consists of a low pass filter (R12 and C13), a buffer circuit (A5), and an amplifier (A4) used to reduce broadband of a device noise. Since resistors R9 and R10 determine the reliability of gain (=1+R10/R9), they are preferably +/−1% of tolerance with low temperature coefficient. D1 and D2 are diodes for a circuit protection to high voltage input. The second part of the signal condition circuit 204b preferably provides a function of offset compensation (VR2 and VR3) and second amplification (A6). A condenser C17 is preferably selected to make a loop response critically damped. When the signal overshoot and a noise level are greater than input voltage $V_{cc}$, the input voltage $V_{cc}$ is preferably bypassed in the forward direction of a diode D4. When the signal overshoot and a noise level are less than ground voltage, input voltage $V_{cc}$ is preferably bypassed in the backward direction of diode D5.

For a wireless biosensor of FIGS. 9 & 10, a wireless data receiver should be equipped before the signal conditioning. The AM wireless receiver 204c in FIG. 20 takes the incoming wireless signal and demodulates the frequency into the corresponding voltage in the even circuit 204d. The signal can be conditioned in the same manner as the non-wireless circuits of 204a and 204b. Other wireless communication skills such as Bluetooth can accommodate the wireless data transmission.

Figure 21:
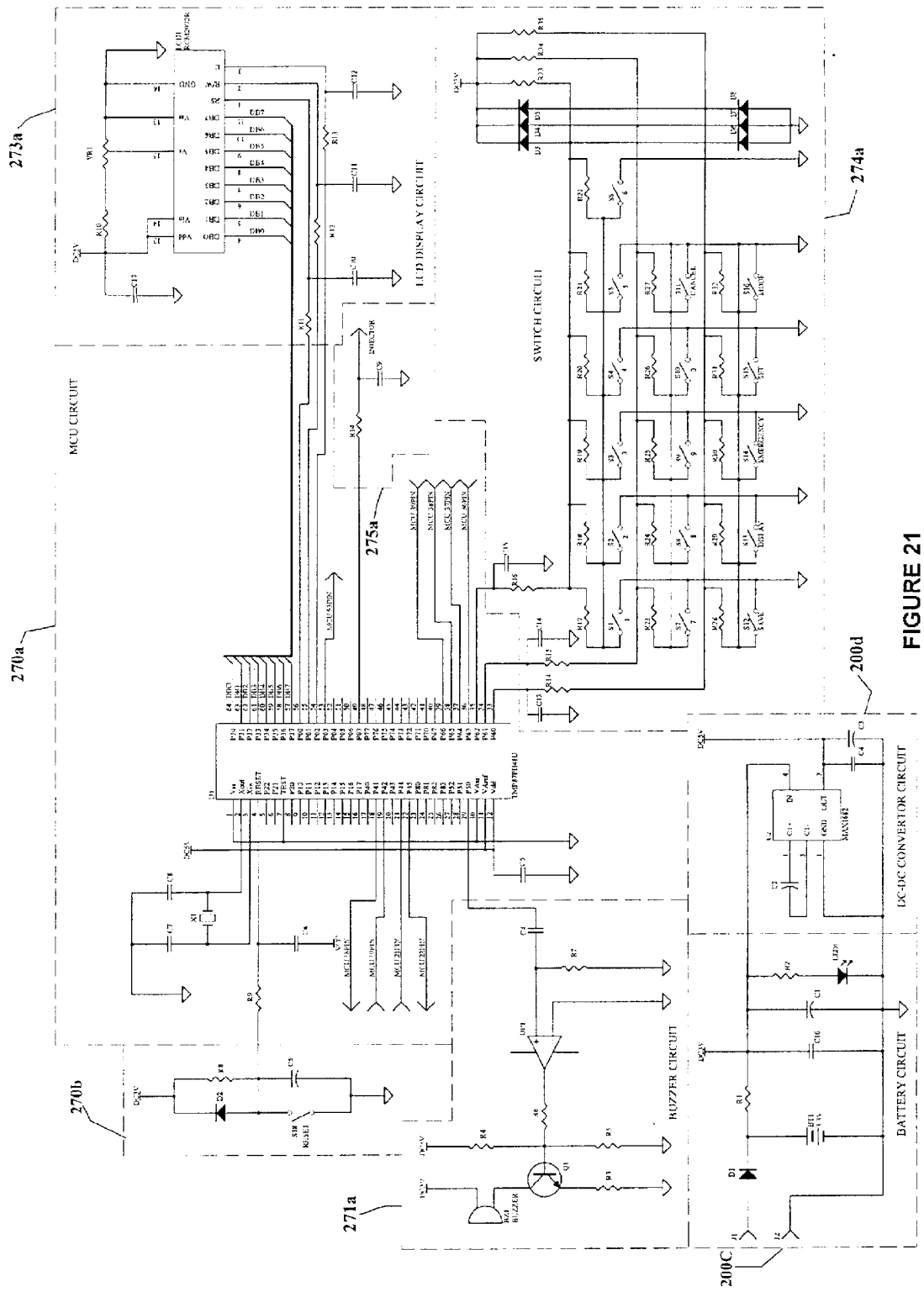
FIG. 21 depicts a circuit for a micro-control unit of the alarm system of FIG. 17.
Figure 22:
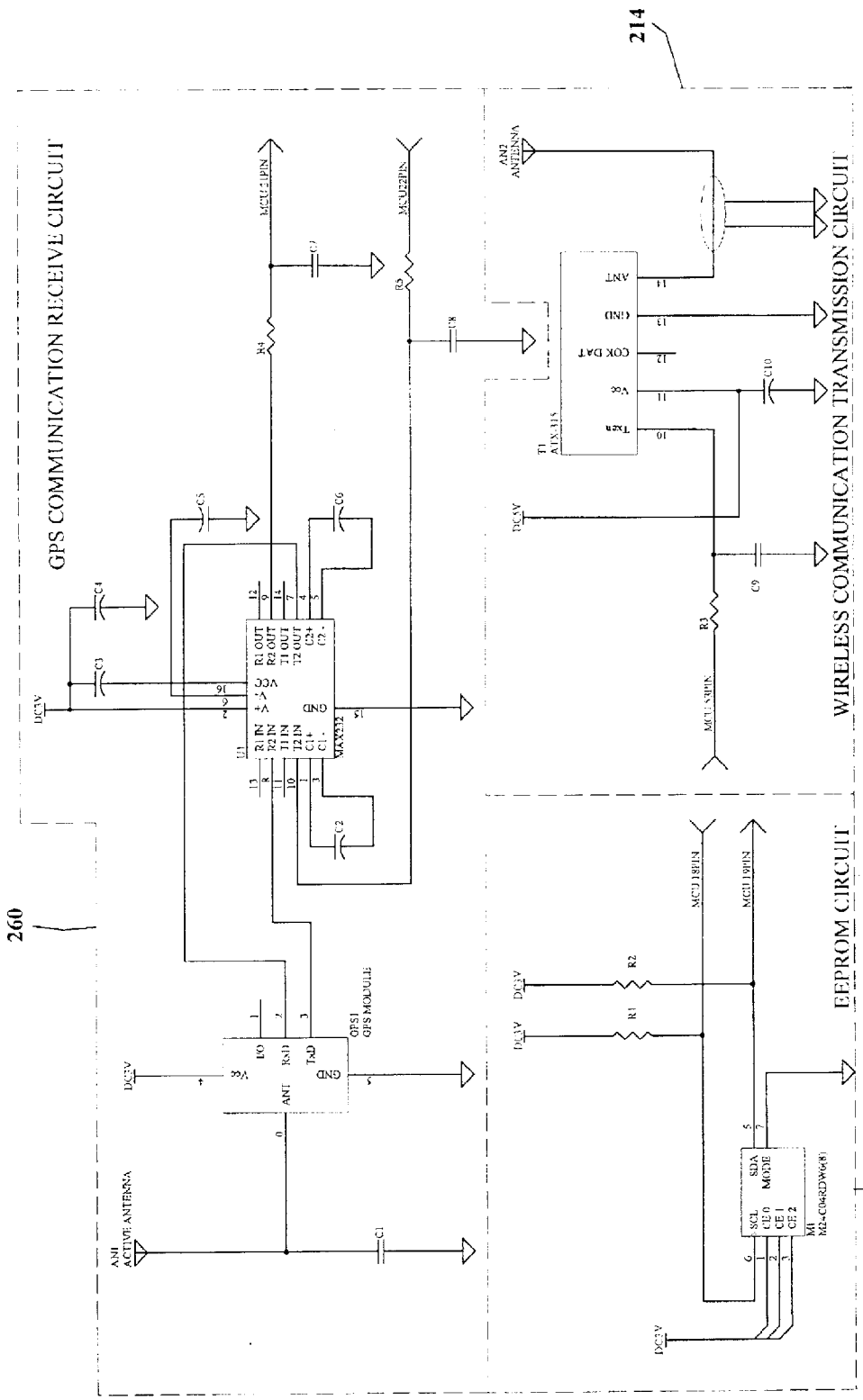
FIG. 22 depicts circuits for the GPS and communications transmitters of the alarm system of FIG. 17.

The functions of the control unit are to compare the input sensor signal with the pre assigned reference signal, to determine the alarm status, to store new value of sensor signal, to retrieve the stored values in memory, to engage with data transmitter for emergency contact, to activate injection device, to initiate alarming buzzer, and to respond key input from patients. As a primary control device in the automatic alarm system, an 8-bit microprocessor is preferably used for every transaction of the automatic alarm system. An assembler and/or a computer language like C language preferably code the transaction, which is compiled for the implementation of microprocessor in hand. The primary function of the microprocessor is to establish real-time monitoring and automatic alarm informing system. An 8-bit microprocessor having low power consumption can supervise the real-time monitoring activity and the automatic alarm system. TMP87CH48 of TOSHIBA 270a in FIG. 21 is preferably selected for the purpose. Alarm status, GPS location code, and signal itself from a sensor can be stored in the memory semiconductor such as flash memory, SRAM, DRAM, or EEPROM. 8K byte of EEPROM 272 in FIG. 22 is preferably selected for the purpose.

Patients can manually operate the automatic alarm device by pushing the key such as reset, signal value display, location code display, and other assigned user functions. The control unit recognizes and interprets key input of a voltage level depending on which key users hit to accomplish the function in hand. The display with a displaying capacity of 20 characters and 2 lines is preferably TN type of LCD or RCM2072R of ROHM 273a in FIG. 21. The extra control functions are the deactivation of the device and the reset 270b of the device in a case when alarms are sent mistakenly or by device malfunctions.

Through the monitoring functions of the control unit, patient's information is preferably continuously transferred to data transmitter in case of emergency. The patient's information preferably includes patient's code of identification, alarm status, GPS location code of X,Y,Z, and a current physiological value from a sensor. In addition, the control unit has the facility to provide output pulse signal 275a to initiate an injection device for immediate emergency care, and activates an alarming buzzer 271a. The injection device is activated when the microprocessor turns on analog output circuit from 'high' to 'low' or 'low' to 'high' as a function '0' and '1'.

A transmitter is necessary in order to operate a wireless communication. The candidate for communication device are a phone including a portable wireless communication device, which can accommodate external data port for exchanging data with the automatic alarm system and inform alarm status and data automatically to a predetermined devices in remote location. Cable and connector can preferably make the connection between data transmitter and automatic alarm system. The selection of cable and connector depends on the wireless data communication device in concern. In addition, wireless connection like Bluetooth can preferably accomplish data transfer between the devices in concern. Alarm status, location information, and other essential information from the automatic alarm system can be transmitted in the form of voice message or text message depending on devices in remote. The wireless communication device is preferably a wireless personal phone supporting CDMA, TDMA, GSM, and other wireless communication standards in operation. PDA (Personal Digital Assistance) with remote Internet service can preferably be other form of wireless portable communication device.

Typically, a transmitter 214 in FIG. 22 consists of a carrier wave generator, a signal generator, a modulator to mix signal to carrier wave, a power booster, and a radiator. The carrier wave frequency may be in the range of several tens to several hundreds megahertz (MHz). The signal picked up from a receiver must be unique to avoid mistaken transmittal due to environmental noises from other electronic devices. Either AM or FM wireless communication can be applied in the automatic alarm system, employing the appropriate communication protocol, and matching an AM or FM receiver also designed to receive the data from the transmitter 214.

The primary function of the GPS unit in FIG. 17 is to provide location data to the recipient(s) of the alarm in the event that the patient carrying the automatic alarm device either does not know his/her location or is unconscious or otherwise unable to describe his location. A GPS receiver 260 supporting NMEA protocol in FIG. 22 is preferably used in the automatic alarm system. The receiver gives a location coordinate of X, Y, Z in a binary form, and the code is transferred to control unit by a conventional RS232C serial communication. The GPS receiver is normally in a standby mode, and automatically activated to inform the caretakers of his/her current location when a patient is in a critical condition.

Figure 23:
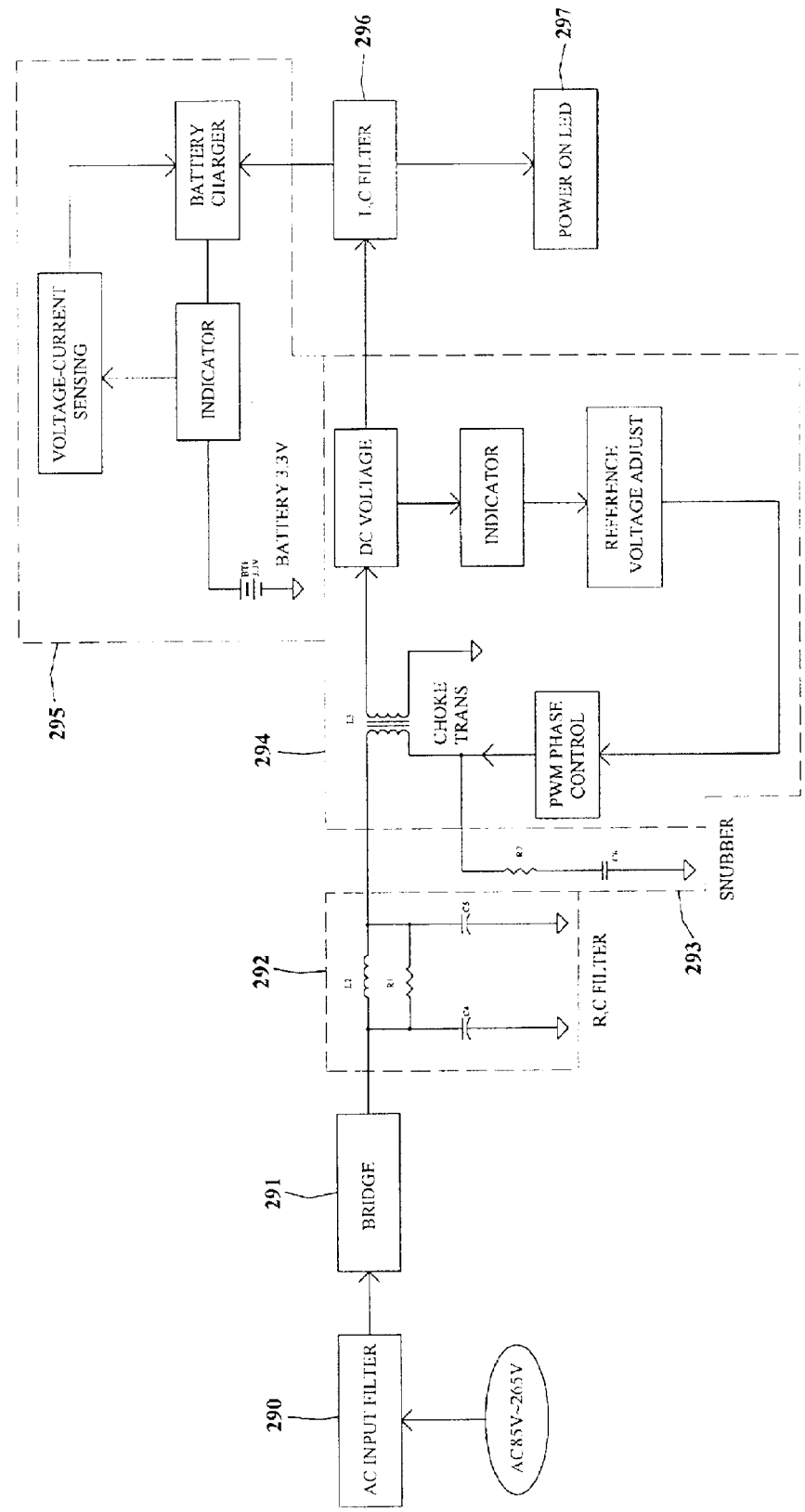
FIG. 23 is a block diagram of a power supply unit for the alarm system of FIG. 17.
Figure 24:
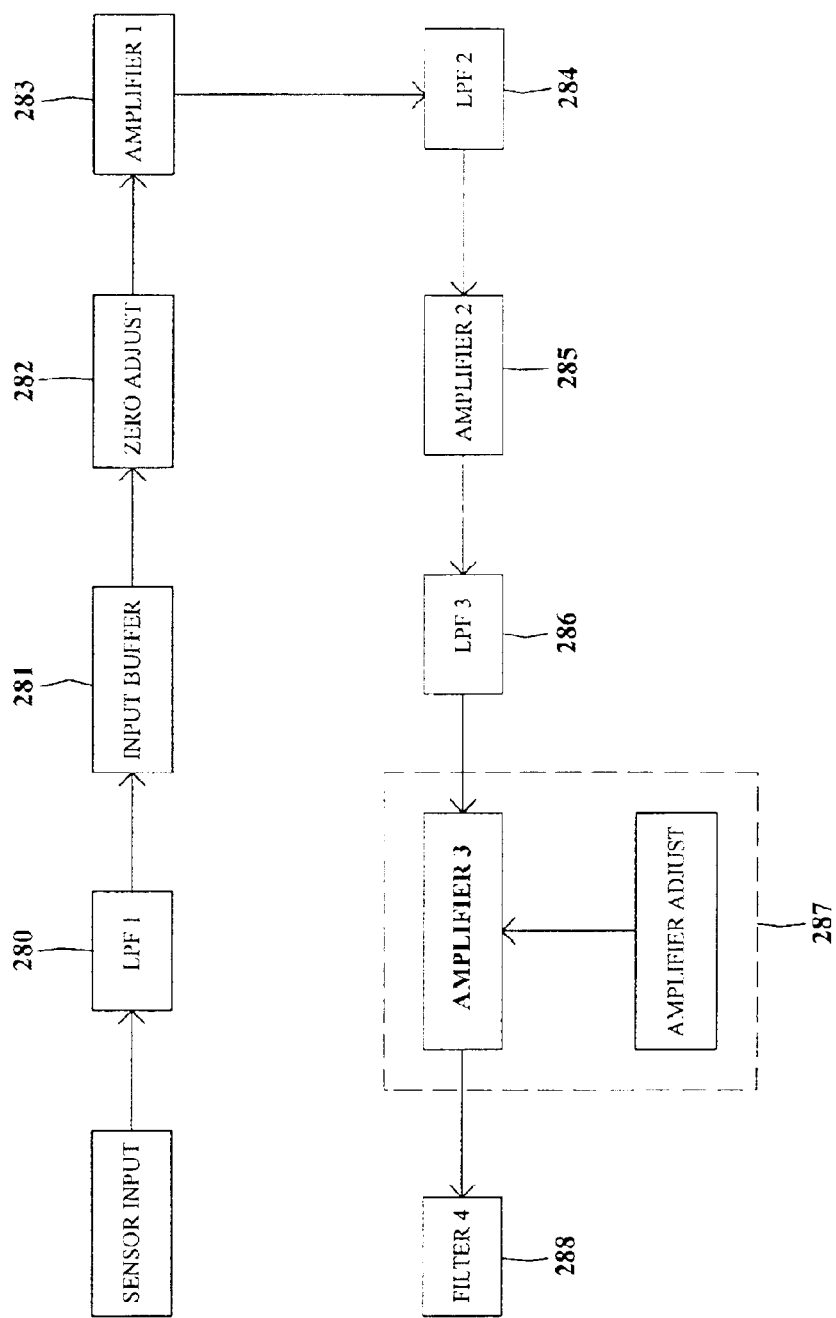
FIG. 24 is a block diagram of a signal conditioner for the alarm system of FIG. 17.
Figure 25:
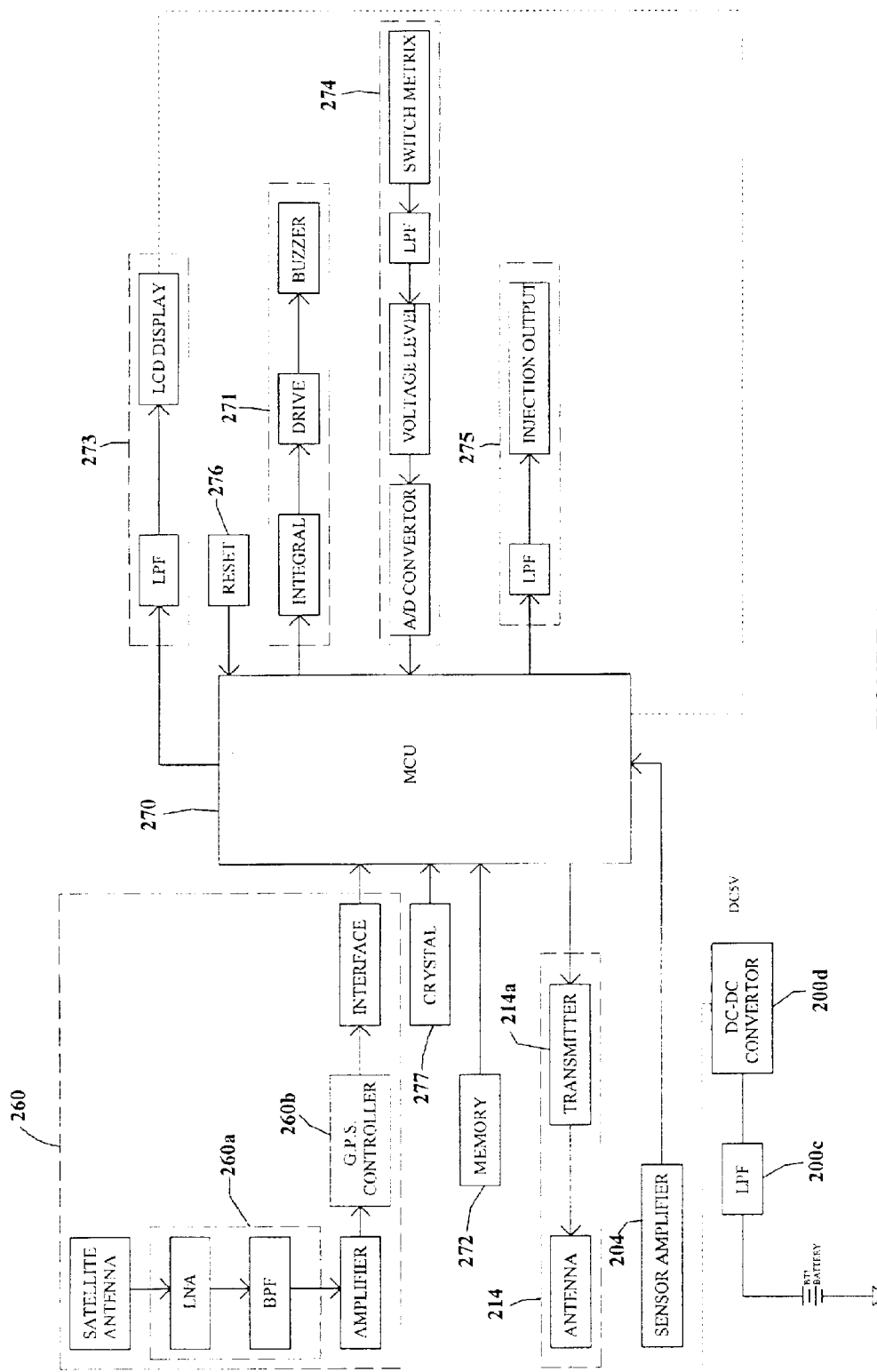
FIG. 25 is a block diagram of the micro-control unity for the alarm system of FIG. 17.

FIGS. 23, 24 and 25 are block diagrams of three major components of the automatic alarm system for a prototype device. FIG. 23 shows a switch mode power supply (SMPS) and charger; FIG. 24 shows a signal conditioning circuit, and FIG. 25 depicts the overall control unit.

As seen in FIG. 25 which is a block diagram of a free voltage input S.M.P.S. circuit and charger block, AC power noise is filtered in an AC input filter 290 before bridge circuit 291 in which AC power (AC 85 V to 265 V) is converted to all wave. RC filter circuit 292 converts the all wave into DC power at the same time DC power noise is filtered. Nevertheless, the converted DC power has spark noise and can be preferably removed by using of snubber circuit 293. The level of converted DC voltage can be preferably adjusted in a adjustment circuit 294 between 4.5 V and 5 V, which is usually a little higher than the voltage capacity of battery to be charged. The converted DC power voltage is preferably filtered by LC filter 296 to reduce the noise generated during the adjustment of DC voltage level. The battery charging circuit 295 controls the charging current and voltage, depending on how much the rechargeable battery is being charged.

A block diagram of the signal conditioner is presented in FIG. 24. The signal level from a sensor is very low and vulnerable to environmental noise. Before amplification the low level signal is preferably filtered by a RC filter, low pass filter 1 (LPF1), 280. Otherwise, both signal and noise are amplified and the signal cannot be distinguished from the noise. The filtered signal is preferably amplified with a gain of approximately 10. The higher amplification gain for the low levels of signal possibly deteriorates the signal and is unable to restore the signal from the noise. The amplified signal is filtered by conventional RC filter (LPF2) 284 to reduce noises again. As the secondary amplification in amplifier2 285, an approximate gain of 100 is preferably engaged to give an enough dynamic range of the A/D converter in the control unit, and the noise filter, LPF3 286 is also used for reducing noises. Although the total amplification gain of the previous amplifiers should be 1000, 10 multiplied by 100, the total gain of 1000 cannot be achieved in a practical sense. The reason is that the devices such op-amps, resistors, and capacitors have their own errors. In order to compensate this discrepancy in gain, a variable resistor should be preferably adjusted in the amplifier adjustment circuit 287. The total amplification gain can be adjusted by an initial input signal from a sensor. Desirably, a surge filter 288 is included to prevent damage from voltage surges.

As shown in the block diagram of FIG. 25, a microprocessor control unit (MCU) 270 preferably controls all devices of a GPS receiver 260, a wireless communication device 214, a signal conditioner 204, a buzzer and recorded voice 271, a memory 272, a display 273, a key in 274, an auto injection device 275, and reset 276. It operates under the designated speed, which can be determined by the crystal 277. MCU 270 can access to memory for storing and retrieving data, which are needed to operate the automatic alarm system. The user can initialize MCU 270 by engaging reset switch 276. Reset 276 will make MCU 270 along with the whole system return to the initial condition, as if the system is turned off and turned on again. The MCU can preferably display information in the automatic alarm system on the LCD (Liquid Clear Display) 273. Users can command MCU 270 by the pre assigned key inputs 274, which are preferably detected by voltage level. The signals bearing location code from GPS satellites 261 are preferably firsthand filtered by BPF(Band Path Filter) 260a with the 20 MHz of bandwidth and 1575.42 MHz of center frequency, which is a nominal frequency band of GPS. Since the signals from the satellites 261 are received as a form of coded data, they should be decoded in GPS controller module 260b. The decoded coordinate data of X/Y/Z directions are then transferred to MCU 270 by RS232C serial communication. The analog signal from signal conditioner 204 is converted to digital signal by MCU 270, which has the A/D converter inside. The digital signal is utilized for comparing predetermined threshold to monitor patient's condition. The output signal of MCU 270 to activate alarming buzzer 271 preferably passes a current drive 271a to control sound level. Along with alarming sound, when critical condition is detected, MCU 271 provides an activated signal to an automatic injection device 275 in concern. On alarm, the recorded and input information as well as location coordinates of patient are transmitted to a pre-determined destination by using a communication device 214. A wireless communication device 214 is preferably used for an automatic alarm informing system. While the invention has been described with reference to at least one preferred embodiment, it is to be clearly understood by those skilled in the art that the invention is not limited thereto. Rather, the scope of the invention is to be interpreted only in conjunction with the appended claims.

Those skilled in the art will appreciate that the combination of a biosensor, an automated alarm notification system with GPS information, and an emergency treatment system (an automatic injection system) provide significant advantages for improving health care. Not only is the patient warned of a condition, which can cause physiological damage, but also health care workers are notified with the updated location information of the patient if the situation surpasses a predetermined threshold. For example, if the diabetic has gone into a hypoglycemic shock, medical personnel (or relatives of the patient) can respond and provide appropriate medical care. Such a system is particularly advantageous for those who live alone and those of limited mobility. The embodiment including a GPS unit is particularly valuable for travelers, as the caretakers to whom the alarm is sent will also receive information about the patient's location While the invention has been described with reference to at least one preferred embodiment, it is to be clearly understood by those skilled in the art that the invention is not limited thereto.

What is claimed is:

1. A biosensor for measuring the concentration of a free analyte in a body fluid, comprising:

a polymeric hydrogel filament that changes its displacement in proportion to the concentration of the free analyte; a photoreceptor arranged in relation to the polymer hydrogel filament so that the intensity of light received by the photoreceptor varies with the displacement of the polymer hydrogel filament; and means for reporting a data signal reflective of the measured light intensity on the photoreceptor.

2. The biosensor of claim 1, additionally including a source of light directing light toward the hydrogel filament.

3. A biosensor for measuring the concentration of a free analyte in a body fluid, comprising:

a polymeric hydrogel filament that changes its displacement in proportion to the concentration of the free analyte; a photoreceptor arranged in relation to the polymer hydrogel filament so that the intensity of light received by the photoreceptor varies with the displacement of the polymer hydrogel filament; a source of light directing light toward the photoreceptor with the hydrogel filament positioned between the source of light and the photoreceptor to block a portion of the light from the source of light directed to the photoreceptor, the amount of light blocked depending upon the displacement of the hydrogel filament; and means for reporting a data signal reflective of the measured light intensity on the photoreceptor.

4. The biosensor of claim 3, wherein the hydrogel filament has one end that moves with the displacement of the hydrogel filament, and wherein the end of the hydrogel filament is positioned between the source of light and the photoreceptor so that movement of the end of the hydrogel filament varies the amount of light blocked.

5. The biosensor of claim 4, further including computing means responsive to the data signal for determining the concentration of the free analyte.

6. The biosensor of claim 5, wherein the computing means compares the data signal to a calibration curve to determine the concentration of the free analyte in the body fluid and produce an output signal representing the free analyte concentration.

7. The biosensor of claim 5, wherein the analyte whose concentration is to be measured is glucose, and wherein the computing means compares the data signal to a calibration curve to compute a concentration of the free glucose in the body fluid and produce an output signal representing the free glucose concentration.

8. The biosensor of claim 2, wherein the photoreceptor is positioned to receive light reflected from the light source by the hydrogel filament, the amount of reflected light received by the photoreceptor depending upon the displacement of the hydrogel filament.

9. A biosensor for measuring the concentration of a free analyte in a body fluid, comprising:
a polymeric hydrogel filament that changes its displacement in proportion to the concentration of the free analyte; a photoreceptor arranged in relation to the polymer hydrogel filament so that the intensity of light received by the photoreceptor varies with the displacement of the polymer hydrogel filament; a source of light directing light toward the hydrogel filiment; reflective material arranged on the hydrogel filament to move with displacement of the hydrogel filament and to reflect light from the source of light toward the photoreceptor, movement of the reflector changing the intensity of light reflected to the photoreceptor; and means for reporting a data signal reflective of the measured light intensity on the photoreceptor.

10. The biosensor of claim 9, wherein the hydrogel filament has one end that moves with the displacement of the hydrogel filament, and wherein the reflective material is positioned on the end of the hydrogel filament.

11. The biosensor of claim 10, further including computing means responsive to the data signal for determining the concentration of the free analyte.

12. The biosensor of claim 11, wherein the computing means compares the data signal to a calibration curve to determine the concentration of the free analyze in the body fluid and produce an output signal representing the free analyte concentration.

13. The biosensor of claim 11, wherein the analyte whose concentration is to be measured is glucose, and wherein the computing means compares the data signal to a calibration curve to compute a concentration of the free glucose in the body fluid and produce an output signal representing the free glucose concentration.

14. The biosensor of claim 1, further including computing means responsive to the data signal for determining the concentration of the free analyte.

15. The biosensor of claim 14, wherein the computing means compares the data signal to a calibration curve to determine the concentration of the free analyte in the body fluid and produce an output signal representing the free analyte concentration.

16. The biosensor of claim 15, wherein the analyte whose concentration is to be measured is glucose and wherein the computing means compares the data signal to a calibration curve to compute a concentration of the free glucose in the body fluid and produce an output signal representing the free glucose concentration.

17. A biosensor for measuring the concentration of glucose, in a body fluid, comprising:
a polymeric hydrogel filament that changes its displacement in proportion to the concentration of glucose; a photoreceptor arranged in relation to the polymer hydrogel filament so that the intensity of light received by the photoreceptor varies with the displacement of the polymer hydrogel filament; a battery powered telemeter for reporting a data signal reflective of the measured light intensity on the photoreceptor, receiving means positioned at a location remote to the patient for receiving the data signal; and computing means responsive to the data signal to compare the data signal to a calibration curve to compute a concentration of the free glucose in the body fluid and produce an output signal representing the free glucose concentration.

18. The biosensor of claim 17, further including computing means operably associated with the receiving means for comparing the data signal to a calibration curve to compute a concentration of the free glucose in the body fluids and produce an output signal representing the glucose concentration.

19. The biosensor of claim 18, wherein the computing means is further configured to compare the detected glucose concentration to a predetermined safe range, and to produce an alarm signal when the detected glucose concentration falls outside the safe range.

20. A biosensor for measuring the concentration of a free analyte in a body fluid, comprising:
a polymeric hydrogel filament that changes its displacement in proportion to the concentration of the free analyte and disposed within a rigid enclosure with at least one area permeable to contact between the hydrogel filament and a fluid being tested and permitting free analyte molecules to diffuse into the filament from the fluid; a photoreceptor arranged in relation to the polymer hydrogel filament so that the intensity of light received by the photoreceptor varies with the displacement of the polymer hydrogel filament; and means for reporting a data signal reflective of the measured light intensity on the photoreceptor.

21. The biosensor of claim 20, wherein the permeable area is an open end in the rigid enclosure, and said open end is sealed by a semipermeable membrane that allows the free glucose molecules to diffuse into the hydrogel.

22. The biosensor of claim 20, wherein the enclosure is conjugated with heparin and polyethylene glycol.

23. The biosensor of claim 20, wherein the enclosure is coated with a semipermeable membrane and a biodegradable polymer on the semipermeable membrane.

24. The biosensor of claim 1, wherein the polymeric hydrogel includes analyte binding molecules (ABM) immobilized in the hydrogel, and analyte molecules immobilized in the hydrogel.

25. The biosensor of claim 24, wherein the analyte binding molecule is a glucose binding molecule (GBM) and the immobilized analyte is a hexose saccharide or a polysaccharide.

26. The biosensor of claim 25, wherein the GBM is either boronic acid, GOX, hexokinase, glucosidase, xylose isomerase, glucose phosphorylase, lactate dehydrogenase, or lectins.

27. The biosensor of claim 25, wherein the GBM molecules include genetically modified proteins which have only binding affinity to glucose moieties but having no enzymatic activity.

28. The biosensor of claim 25, wherein the hexose saccharide has a vinyl group conjugated to the Cl hydroxyl group of the hexose saccharide and is selected from the group that consists of a-D-mannopyranoside, p-nitrophenyl-a-D-mannopyranoside, or p-nitrophenyl-a-D-glucopyranoside.

29. The biosensor of claim 25, wherein the hexose saccharide include monomer containing hexose moieties selected from the group consisting of glycidyl acrylate, glycidyl butyl ether, glycidyl cinnamate, or glycidyl methacylate such as glycosyloxyethyl methacrylate.

30. The biosensor of claim 25, wherein the polysaccharide chemically or physically immobilized in the hydrogel filament is any macromolecule that contains polysaccharides.

31. The biosensor of claim 25, wherein the immobilized glucose molecules and immobilized GBM are present at respective cross-linking densities chosen to optimize the amount of hydrogel swelling in response to changes in level of free glucose molecules.

32. The biosensor of claim 24, wherein the analyte binding molecule is selected from the group consisting of: antibodies, enzymes, membrane receptors, kinases, Protein A, Poly U, Poly A, Poly lysine, triazine dye, nucleoside, thiol, heparin, polysaccharides, Coomassie blue, azure A, and metal-binding peptides, proteins, and chelating agents.

33. The biosensor of claim 24, wherein the immobilized analyte is selected from the group consisting of: antigens, enzyme cofactors, enzyme substrates, enzyme inhibitors, IGG, sugar, carbohydrate, nucleic acids, nucleotide, nucleoside, cysteine, arginine, lysine, protamine, heparin, dyes, and metal ions.

34. A biosensor for measuring the concentration of a free analyte in a body fluid, comprising:
a polymeric hydrogel filament that chances its displacement in proportion to the concentration of the free analyte; a photoreceptor arranged in relation to the polymer hydrogel filament so that the intensity of light received by the photoreceptor varies with the displacement of the polymer hydrogel filament; means for reporting a data signal reflective of the measured light intensity on the photoreceptor; a reference polymeric hydrogel filament similar to the hydrogel filament but which does not change its displacement in response to the concentration of the free analyte; a reference photoreceptor arranged in relation to the reference polymer hydrogel filament so that the intensity of light received by the photoreceptor varies with the displacement of the reference polymer hydrogel filament; means for reporting a reference data signal reflective of the measured light intensity on the reference photoreceptor, and means for compensating the data signal in respones to changes in the reference data signal to compensate for any change in the data signal attributable to factors other than the analyte concentration.

35. A sensor for measuring the concentration of free molecules of an analyte in a fluid, comprising:
a rigid enclosure having an open end and a closed end, the open end being covered by a semipermeable membrane adapted to be placed in the fluid;
a hydrogel positioned within the enclosure between the semipermeable membrane and the closed end, said hydrogel changing its displacement in the enclosure depending upon analyte concentration in the fluid; and
a photoreceptor positioned with respect to the enclosure so that changes in displacement of the hydrogel are accompanied by changes in light intensity detected by the photoreceptor.

36. The sensor of claim 35, including a battery powered telemeter operatively engaged to the photoreceptor.

37. The sensor of claim 35, wherein the hydrogel changes its displacement depending upon the glucose concentration in the fluid, whereby the light intensity detected by the photoreceptor is indicative of the glucose concentration in the fluid.

38. A method of determining the concentration of free analyte in a fluid, comprising the steps of:
providing a hydrogel filament having pendant charged or uncharged moieties, analyte molecules, and analyte-specific binding molecules covalently immobilized therein so that the hydrogel filament will swell to varying degrees upon exposure to varying concentrations of analyte;
enclosing the hydrogel in a rigid structure which has at least one permeable portion for contacting the fluid, the permeable portion permitting free analyte in the fluid to diffuse into the hydrogel, the rigid structure allowing displacement of the hydrogel therein in response to the swelling of the hydrogel in response to analyte concentration in the fluid;
positioning a photoreceptor with respect to the rigid structure so that light intensity on the photoreceptor varies with displacement of the hydrogel;
inserting the permeable portion of the biosensor into the fluid and allowing sufficient time for free analyte molecules to diffuse to equilibrium within the hydrogel;
sensing the light intensity on the photoreceptor and providing a data signal reflective thereof, which is also reflective of the displacement of the hydrogel; and
comparing the sensed hydrogel displacement with a calibration curve to determine analyte concentration of the test fluid.

39. The method of claim 38, wherein the step of comparing the sensed hydrogel displacement with a calibration curve includes the step of providing computing means connected to receive the data signal, compare it to a predetermined calibration curve of displacement change vs. concentration of free analyte molecules, and output a concentration value.

40. The method of claim 38, wherein the step of providing a hydrogel having analyte molecules and analyte-specific binding molecules is the step of providing a hydrogel having glucose molecules and glucose-specific binding molecules whereby the analyte whose concentration is sensed is glucose.

* * * * *